(12) United States Patent
Weidner et al.

(10) Patent No.: US 8,426,475 B2
(45) Date of Patent: Apr. 23, 2013

(54) TREATMENT OF CONNECTIVE TISSUE DISEASES OF THE SKIN

(75) Inventors: Morten Sloth Weidner, Virum (DK); Hans Christian Wulf, Epsergaerde (DK)

(73) Assignee: Astion Development A/S, Copenhagen O (DK)

(*) Notice: Subject to any disclaimer, the term of this patent is extended or adjusted under 35 U.S.C. 154(b) by 1273 days.

(21) Appl. No.: 11/402,255

(22) Filed: Apr. 12, 2006

(65) Prior Publication Data

US 2006/0235048 A1 Oct. 19, 2006

(51) Int. Cl.
*A01N 31/08* (2006.01)
*A01N 31/00* (2006.01)
*A61K 31/05* (2006.01)
*A61K 31/045* (2006.01)

(52) U.S. Cl.
USPC .......................................... 514/731; 514/738

(58) Field of Classification Search .................. 514/731, 514/738
See application file for complete search history.

(56) References Cited

U.S. PATENT DOCUMENTS

| | | | |
|---|---|---|---|
| 4,088,756 A | 5/1978 | Voorhees | |
| 4,284,623 A * | 8/1981 | Beck | 424/157.1 |
| 4,574,129 A | 3/1986 | Nair et al. | |
| 4,699,777 A | 10/1987 | Zupon et al. | |
| 4,975,466 A | 12/1990 | Bottcher et al. | |
| 4,980,159 A | 12/1990 | Koslo | |
| 5,648,386 A | 7/1997 | Resemann et al. | |
| 5,795,564 A | 8/1998 | Aberg et al. | |
| 5,919,827 A | 7/1999 | Barberich et al. | |
| 6,068,833 A | 5/2000 | Aberg et al. | |
| 6,110,974 A | 8/2000 | Aberg et al. | |
| 6,114,389 A * | 9/2000 | Bouras | 514/574 |
| 6,254,882 B1 | 7/2001 | Jerussi | |
| 6,267,972 B1 | 7/2001 | Breton et al. | |
| 6,437,165 B1 * | 8/2002 | Mandala et al. | 558/169 |
| 2003/0236298 A1 | 12/2003 | Meng et al. | |
| 2004/0220153 A1 | 11/2004 | Jost-Price et al. | |
| 2004/0220237 A1 | 11/2004 | Fu et al. | |
| 2004/0224876 A1 | 11/2004 | Jost-Price et al. | |
| 2005/0130935 A1 | 6/2005 | Weidner | |
| 2005/0192261 A1 | 9/2005 | Jost-Price et al. | |

FOREIGN PATENT DOCUMENTS

| | | |
|---|---|---|
| GB | 2 255 503 A | 11/1992 |
| WO | WO 95/19336 | 7/1995 |
| WO | WO 03/048122 A2 | 6/2003 |
| WO | WO 03/088997 A2 | 10/2003 |
| WO | WO 03/092617 A2 | 11/2003 |
| WO | WO 03/097073 A1 | 11/2003 |
| WO | WO 03/104204 A1 | 12/2003 |
| WO | WO 2004/073614 A2 | 9/2004 |
| WO | WO 2005/004852 A1 | 1/2005 |
| WO | WO 2005/102296 A2 | 4/2005 |
| WO | WO 2005/051293 A2 | 6/2005 |
| WO | WO 2005/079284 A2 | 9/2005 |
| WO | WO 2005/089741 A2 | 9/2005 |
| WO | WO 2006/027579 A2 | 3/2006 |

OTHER PUBLICATIONS

Pullen, Jr., R.; "Managing subacute cutaneous lupus erythematosus" Dermatology Nursing, Dec. 2001, pp. 1-3.*
Freitas et al. "Chronic cutaneous Lupus erythematosus: sudy of 290 patients", An bras Dermatol, Rio de Janeiro, 2003, vol. 78(6), pp. 703-771.*
Patent Abstract of Japan, 07258067 A, Oct. 9, 1995.
Patent Abstracts of Japan, 07304647 A, Nov. 21, 1995.
Patent Abstracts of Japan, 09110674 A, Apr. 28, 1997.
Patent Abstracts of Japan, 63010716 A, Jan. 19, 1988.
Dawn Baramki BSN et al.; "Modulation of T-cell function by (R)- and (S)-isomers of albuterol: Anti-inflammatory influences of (R)-isomers are negated in the presence of the (S)-isomers", J. Allergy Clin. Immunol. 2002, 109(3):449-454.
Peter J. Barnes, "Effect of beta-agonists on inflammatory cells", J. Allergy Clin. Immunol. 1999, 104(2 Pt 2):510-517.
Richard Kalish et al., "Sensitization of mice to topically applied drugs: albuterol, chlorpheniramine, clonidine and nadolol", Contact Dermatitis, 1995, 35, pp. 76-82.
Karen E. McCrea et al., "Salmeterol, a long acting beta$_2$-adrenoceptor agonist mediating cyclic AMP accumulation in a neuronal cell line", Br. J. Pharmacol. 1993, 110: 619-626.
Philip J. Thompson et al., "Shrinking Lungs, Diaphragmatic Dysfunction, and Systemic Lupus Erythematosus[1,2]", Am. Rev. Respir. Dis. 1985, 132(4):926-928.
Biochemical Modulation of Skin Reactions, pp. 10-11, edited by Agis K. Kydonieus and John J. Wille, CRC Press LCC 2000.
Rooks, Textbook of Dermatology, Chapter 65, pp. 56.2-56.4, vol. 3, 7th edition, edited by Tony Burns et al., Blackwell Science, 2004.
Seong. H. Cho et al., "(S)-Albuterol Increased the Production of Histamine and IL-4 in Mast Cells", Int'l. Archives of Allergy & Immunol. 2001: 124:478-484, 2000.
Dean Handley, PhD, "The asthma-like pharmacology and toxicology of (5)-isomers of beta agonists", J. Allergy Clin Immunol. 1999, 104(2 Pt 2):S69-S76.
Clive P. Phage PhD et al., "Contrasting properties of albuterol stereoisomers", J. Allergy Clin. Immunol. 1999, 104(2 Pt. 2):S31-S41.
L. J. Petersen et al., "The effect of salmeterol and salbutamol on mediator release and skin responses in immediate and late phase allergic cutaneous reactions", Inflamm. Res. 48 (1999) 528-532.
Joseph L. Rau PhD, "Introduction of a Single Isomer Beta Agonist", Respiratory Care, Aug. 200, vol. 45, No. 8, pp. 962-966.

(Continued)

*Primary Examiner* — Sreeni Padmanabhan
*Assistant Examiner* — Kendra D Carter
(74) *Attorney, Agent, or Firm* — Foley & Lardner LLP

(57) ABSTRACT

The present invention provides effective and safe medicaments for the treatment of connective tissue diseases of the skin, particularly with respect to the treatment of cutaneous forms of Lupus Erythematous. The medicaments comprise as the therapeutically active ingredient a beta$_2$ adrenoceptor agonist. The invention furthermore relates to dermatological compositions without skin sensitization properties and which contain enantiomerically pure or enriched R-enantiomers of a beta$_2$ adrenoceptor agonist.

5 Claims, No Drawings

OTHER PUBLICATIONS

Catherine D. Strader et al. "Identification of Two Series Residues Involved in Agonist Activation of the β-Adrenergic Receptor", The Journal of Biological Chemistry, vol. 264, No. 23, Aug. 15, 1989, pp. 13572-13578.

Michelle L. Harris et al., "Autoimmunity in scleroderma: the origin, pathogenetic role, and clinical significance of autoantibodies", Cur Opin Rheumetol 15:778-784, 2003.

D. Slattery et al., "Levalbuterol Hydrochloride", Pediatric Pulmonology 33:151-157 (2002).

Michelle L. Harris et al., "Autoimmunity in scleroderma: the origin, pathogenetic role, and clinical significance of autoantibodies", Curr Opin Reumatol 15: 778-784, 2003.

Catherine D. Strader et al., "Identification of Two Serine Residues Involved in Agonist Activation of the β-Adrenergic Receptor", The Journal of Biological Chemistry vol. 264, No. 23, Issue of Aug. 15, pp. 13572-13578, 1989.

FJ Munoz Rodriguez et al., "Shrinking lungs syndrome in systemic lupus erythematosus: improvement with inhaled beta-agonist therapy", Lupus (1997) 6, 412-414.

Israeli Office Action Patent Application No. 186491 dated Jan. 21, 2010.

* cited by examiner

TREATMENT OF CONNECTIVE TISSUE DISEASES OF THE SKIN

FIELD OF THE INVENTION

The present invention relates to the field of pharmacological science. There is provided novel principles of treating connective tissue diseases of the skin, particularly cutaneous manifestations of Lupus Erythematosus in an individual by administering a $beta_2$-adrenoceptor agonist to the affected skin areas of the individual. Furthermore, the invention is directed to topically administrable compositions comprising a $beta_2$-adrenoceptor agonist in enantiomeric enriched or pure form.

BACKGROUND OF THE INVENTION

There is no permanent cure for connective diseases of the skin, such as cutaneous forms of Lupus Erythematosus. Today, the treatment of connective diseases includes topical treatment with strong steroids, sometimes in combination with anti-malarial drugs or systemic immuno-suppressants. Unfortunately, the treatment with such drug agents has serious side effects and cannot be applied for prolonged periods.

The present inventor has recognised the strong need for therapeutic agents that can effectively alleviate the symptoms of cutaneous forms of Lupus Erythematosus (LE) without exhibiting significant adverse effects. Quite surprising, the present inventor has found that the topical application of a $beta_2$-adrenoceptor agonist effectively relieves the clinical manifestations in cutaneous forms of Lupus Erythematosus.

Cutaneous forms of Lupus Erythematosus (Cutaneous Lupus Erythematosus) encompass at least 10 to 15 different clinical presentations that usually can be divided into 3 categories, including (1) acute cutaneous lupus erythematosus (ACLE), (2) subacute cutaneous lupus erythematosus (SCLE), and (3) chronic cutaneous lupus erythematosus (CCLE). Some of the common types of cutaneous LE include chronic cutaneous lupus erythematosus (CCLE) and various sub-types thereof.

Current evidence indicates that cutaneous Lupus Erythematosus is a separate disease from systemic Lupus Erythematosus and not just a benign variant of systemic LE in that the two diseases seems to be genetically different diseases (Rook's, *Textbook of Dermatology*, chapter 65, page 56.2, volume 3, $7^{th}$ edition, edited by Tony Burns et al, Blackwell Science, 2004). Systemic Lupus Erythematosus (SLE) is the most common connective tissue disease and is characterised by multi-organ inflammation, which most commonly affects the skin, joints and vasculature. Almost any organ or system of the body, including the lungs, kidneys, heart or brain may be affected by the inflammation.

$Beta_2$-adreneroceptor agonists are traditionally used in the treatment of respiratory diseases such as asthma, chronic bronchitis and nervous system injury. $Beta_2$-adrenoceptor agonists has also been found to interact with specific receptors on T-lymphocytes to mediate anti-inflammatory activities (Baramki D et al. Modulation of T-cell function by (R)- and (S)-isomers of albuterol: anti-inflammatory influences of (R)-isomers are negated in the presence of the (S)-isomer. *J Allergy Clin Immunol* 2002 March; 109(3):449-54) and Barnes P J. Effect of beta-agonists on inflammatory cells. *J Allergy Clin Immunol* 1999 August; 104(2 Pt 2):S10-S1)7.

A number of drug agents and combinations thereof have been proposed for the treatment of various inflammatory diseases including discoid Lupus Erythematosus, wherein a $beta_2$-adrenoceptor agonist among other drug agents is proposed to be administered as a secondary active drug agent.

The patent application US2005192261 relates to topical treatment with combinations of an antihistamine or an antihistamine analogue and a corticosteroid.

The patent application WO05051293 relates to topical treatment with Ibudilast or a related compound.

The patent application US2004220153 relates to topical treatment with a selective serotonin reuptake inhibitors (SSRI).

The patent application US2004224876 relates to topical treatment with a non-steroidal immunophilin-dependent immunosuppressant (NsIDI) and an NsIDI enhancer (NsI-DIE).

Notably, none of the above-mentioned patent application relates to the direct treatment of cutaneous forms of LE with a $beta_2$-adrenoceptor agonist, neither as the sole therapeutically agent nor as the primary therapeutically agent.

Furthermore, a number of treatment regimens have been proposed for the treatment of systemic LE. In these treatments, the primary therapeutically effective drug agent eventually may be co-administered with a $beta_2$-adrenoceptor agonist:

The patent application WO2003092617 relates to the treatment of an inflammatory skin disease, such as systemic Lupus Erythematosus, by topically administering a steroid and a beta-adrenergic receptor ligand.

The patent application US2003236298A1 (Atherogenics Pharmaceuticals, Inc) relates to 1,3-bis-(substituted-phenyl)-2-propen-1-ones that are inhibitors of the expression of VCAM-1 for the treatment of patients with a disease mediated by VCAM-1, such as systemic Lupus Erythematosus.

The patent applications US2005130935 and WO 2003097073 (Astion Development A/S) relate to combinations of a $beta_2$-adrenoceptor agonist and an aminosugar for the treatment of inflammatory diseases, including systemic Lupus Erythematosus.

The patent applications US20050176714 and WO2003104204 relate to pyridazine derivatives acting as phosphodiesterase IV inhibitors for the treatment of autoimmune diseases, such as systemic Lupus Erythematosus.

Furthermore, unusual respiratory manifestations of systemic Lupus Erythematosus, "shrinking lungs" have been treated with albuterol (Salbutamol) (Thompson P J, Dhillon D P, Ledingham J, Turner-Warwick M. Shrinking lungs, diaphragmatic dysfunction, and systemic Lupus Erythematosus. *Am Rev Respir Dis.* 132(4), 926-8, 1985).

Topical administration of $beta_2$-adrenoceptor agonists has been shown to result in sensitization of the skin and allergic reactions. For example, salbutamol (albuterol) has been reported to be a topical sensitizer that causes contact dermatitis reactions when applied to the surface of the skin of humans (in *Biochemical Modulation of Skin Reactions*, page 10-11, edited by Agis K. Kydonieus and John J. Wille, CRC Press LCC 2000).

However, the present inventor has overcome this problem by providing topically administrable compositions only or mainly comprising the R-enantiomeric form of a $beta_2$-adrenoceptor agonist.

Topically administrable compositions comprising an enantiomerically pure $beta_2$-adrenoceptor agonist have been disclosed in the art:

The patent application US2005192261 discloses topical compositions primarily comprising an antihistamine or an antihistamine analogue and a corticosteroid.

The patent application WO05051293 (COMBINATORX, INCORPORATED) discloses topical compositions primarily comprising Ibudilast or related compounds.

The patent application US2004220153 discloses topical compositions primarily comprising selective serotonin reuptake inhibitors (SSRI).

The patent application US2004224876 discloses topical compositions primarily comprising a non-steroidal immunophilin-dependent immunosuppressant (NsIDI) and an NsIDI enhancer (NsIDIE).

The patent application WO2003092617 (COMBINATORX, INCORPORATED) discloses topical compositions comprising a steroid and a beta-adrenergic receptor ligand.

Topical compositions of a $beta_2$-adrenoceptor agonist are proposed in several documents, but these fail to emphasise the importance of administering the enantiomeric pure form: The patent application U.S. Pat. No. 4,574,129 (Bristol-Myers Company) discloses topical compositions comprising a $beta_2$-adrenoceptor agonist and vehicle materials for the treatment of topical anti-inflammatory effect in mammals.

The U.S. Pat. No. 4,699,777 (Schering Corporation) discloses transdermal compositions of albuterol further comprising 5 to 50% of 1-dodecyl-azacycloheptan-2-one and 5 to 50% of non-aqueous urea.

The U.S. Pat. No. 4,975,466 (Ciba-Geigy Corporation) discloses topical compositions based on Formoterol and related compounds for use in the treatment of inflammatory skin diseases.

The U.S. Pat. No. 4,980,159 (Bristol-Myers Squibb Company) discloses post-shave compositions (aqueous solutions) comprising a $beta_2$-adrenoceptor agonist for pilomotor effects.

The U.S. Pat. No. 6,267,972 (Societe L'Oreal S. A) discloses cosmetic/pharmaceutical compositions for the treatment of cutaneous diseases and sensitive skin comprising an effective substance P antagonist amount of at least one $beta_2$-adrenoceptor agonist together with an skin irritant.

The patent application WO05102296 (HEPTAGEN LIMITED) discloses topical compositions comprising a combination of vitamin D or an analogue, preform or derivative thereof, a cannabinoid or cannabinoid receptor agonist, and a $beta_2$-adrenoceptor agonist for the treatment of psoriasis.

The patent application WO03088997 (UNIVERSITEIT UTRECHT HOLDING B.V) discloses topical compositions of an antigen and a $beta_2$-adrenoceptor agonist for the induction of tolerance to treat autoimmune diseases, delayed type hypersensitivity reactions and/or transplant rejection, and/or graft versus host reaction and/or allergic reactions.

The patent application US2003236298A1 (Atherogenics Pharmaceuticals, Inc) discloses topical compositions of 1,3-bis-(substituted-phenyl)-2-propen-1-ones inhibiting the expression of VCAM-1.

The patent application US2005130935A1 (Astion Development A/S) discloses combinations of $beta_2$-adrenoceptor agonist and an aminosugar for the treatment of inflammatory diseases.

The patent application JP7304647 (KAO CORP) discloses compositions for massage comprising one or more compounds selected from (A): (i) a xanthine derivative, (ii) a beta-adrenergic agent, (iii) an alpha-2 adrenergic activity inhibitor, and (iv) a bipyridine derivative; and (B) a scrubbing agent.

The patent application JP9110674 (KAO CORP) discloses a bathing composition comprising a compound of the plant of pepper family (e.g. Piper nigrum L, Piper longum L, Piper angustifolium), carbonate and an organic acid.

The patent application JP 61-154201(TEIJIN LTD) discloses transdermal compositions comprising a β-stimulation agent and a dissolution assistant agent.

The patent application JP 06-048497 (Kao Corp) discloses a bathing agent composition containing a β-adrenergic stimulant, inorganic salt, an organic acid and an oily component.

The patent application U.S. Pat. No. 4,088,756 (The Regents of the University of Michigan) relates to topically applied compositions comprising at least one active compound selected from the groups α1, β1, and β2-adrenergic agents and oral hypoglycemic agents.

The patent application WO05102296A2 (HEPTAGEN LIMITED) relates to topically applied compositions comprising vitamin D or its analogue, cannabinoid or a cannabinoid receptor agonist; and a beta-adrenoceptor agonist for the treatment of immuno-proliferative skin diseases.

The patent application WO2003092617 (COMBINATORX, INCORPORATED) relates to topically applied compositions comprising a steroid and a beta-adrenergic receptor agonist for the treatment of an inflammatory skin disease.

The patent application WO9519336 (IOVIS BIOMEDICAL AND PHARMACEUTICAL CONSULTANTS) relates to phenyl ethanol amine ethers acting as beta adrenergic agonists that may be applied topically to skin.

Notably, none of the above-mentioned patents and patent applications disclose topically administrable compositions, wherein the $beta_2$-adrenoceptor agonist is the primary therapeutical agent or the sole therapeutical agent.

SUMMARY OF THE INVENTION

Surprisingly, the present inventor has found that $beta_2$-adrenoceptor agonists (in short "$beta_2$ agonist") have strong therapeutic potential in the treatment of cutaneous forms of Lupus Erythematosus, even when applied as the sole therapeutically active ingredient to a patient with cutaneous LE. Clinical data shown herein clearly demonstrate the significant improvement of inflamed lesions after only 3 weeks treatment with topical Salbutamol to a patient suffering from Discoid Lupus Erythematosus. In another patient diagnosed with Sub-acute Cutaneous Lupus Erythematosus, complete remission of the cutaneous symptoms was observed after 8 weeks of treatment with topical Salbutamol. Notably, these patients have had the diseases for several years, where treatment with strong corticosteroids had only little effect.

Therefore, the present invention provides significant improvements in the treatment of cutaneous forms of LE even in patients that are not responding well to gluco-corticosteroids.

The clinical data are very surprising since cutaneous Lupus Erythematosus are very difficult to treat.

Contrarily to existing therapeutic agents applied in the treatment of cutaneous Lupus Erythematosus, the $beta_2$-adrenoceptor agonists according to the present invention have the advantage of not being likely to be associated with any serious side effects, as these agonists are safe and well tolerated by the organism in pharmacologically relevant doses.

Cutaneous forms of Lupus erythematosus are characterised by patchy dermal lymphocytic infiltrates, where the majority of infiltrating lymphocytes are T-lymphocytes expressing antigens. Without being limited to a particular theory, the present findings of the novel use of $beta_2$-adrenoceptor agonists can be extended to all skin diseases where the pathology, at least in part, involves expression of $beta_2$ receptors in leukocytes, such as in the T-lymphocyte. Typically, such skin diseases presenting dermal lymphocytic infiltrates include all kinds of connective tissue diseases.

Therefore, the present invention relates in a first aspect to a method for the treatment or prevention of cutaneous Lupus Erythematosus or another connective tissue disease affecting the skin in an individual. The method comprises administration to said individual of an effective amount of a therapeutically active ingredient in the form of a beta$_2$-adrenoceptor agonists, a stereoisomer thereof, an enantiomer thereof, a physiologically acceptable derivative thereof, and/or a pharmaceutically acceptable salt thereof. Preferably, the treatment is effected by mono-therapy, wherein no other therapeutically effective ingredient is administered together with the beta$_2$-adrenoceptor agonists. Furthermore, the administration is preferably effected by topical application to skin.

The inventor has furthermore solved the problem with topical sensitization of skin caused by beta$_2$-adrenoceptor agonists by selecting the particular enantiomer that is pharmacologically active and which does not cause sensitization reactions in skin.

Therefore, a second aspect of the invention relates to a topically administrable pharmaceutical composition comprising:

i) a therapeutically active ingredient in the form of enantiomerically enriched or enantiomerically pure R-enantiomer of a beta$_2$-adrenoceptor agonist, a physiologically acceptable derivative thereof or a pharmaceutically acceptable salt thereof; and ii) one or more dermatologically acceptable excipients or carriers.

The therapeutically active ingredient is preferably the sole therapeutically agent, or at least the primary therapeutically active ingredient included in the topically administrable composition.

Where it is desirable to employ additionally therapeutically active ingredients in the methods, medicaments and topically administrable compositions of the invention, the following therapeutically active ingredients are considered as less relevant or suitable for the treatment of connective tissue diseases of the skin and are rather excluded from such methods, medicaments and compositions. Such a therapeutically active ingredient may be selected from a steroid; Ibudilast or a related compound; a selective serotonin reuptake inhibitor (SSRI); a non-steroidal immunophilin-dependent immunosuppressant (NsIDI), an anti-histamine; or an aminosugar).

Topically administrable compositions of this invention have the significant advantage of being devoid of cutaneous atrophy associated with treatment with topical gluco-corticosteroids, which have so far been the mainstay treatment of cutaneous Lupus Erythematosus.

DETAILED DESCRIPTION OF THE INVENTION

The present inventor has recognised the beneficial effect of a beta$_2$ agonist in treating connective tissue diseases, particularly in the treatment of cutaneous forms of Lupus Erythematosus.

Accordingly, a first aspect of this invention relates to a method for the treatment or prevention of a connective tissue disease of the skin, such as cutaneous forms of Lupus Erythematosus. The method comprises administration of a sufficient amount of a beta$_2$ agonist, a stereoisomer thereof, an enantiomer thereof, a physiologically acceptable derivative thereof, and/or a pharmaceutically acceptable salt thereof to the affected skin areas of an individual in need thereof. More particularly, the beta$_2$ agonist may in some embodiments be the sole therapeutically active ingredient to be administered or at least be the primary/first therapeutically active ingredient to be administered.

Thus, the invention is meant to be directed to the prevention, alleviation and treatment of cutaneous manifestations in an individual suffering from or diagnosed with a connective tissue disease of the skin, such as cutaneous forms of Lupus Erythematosus.

As used herein, the phrase "cutaneous forms of Lupus Erythematosus" and "cutaneous Lupus Erythematosus" are meant to be interchangeable phrases encompassing various types of LE that have cutaneous manifestations of the disease in the skin or mucosa of an individual. Such cutaneous forms of LE are typically characterised by the presence of the immunoglobulins IgG, IgA and IgM and complements at the dermal-epidermal junction in skin lesions for 6 weeks or more (Rook's, *Textbook of Dermatology*, chapter 65, pages 56.5 to 56.69, volume 3, 7$^{th}$ edition, edited by Tony Burns et al, *Blackwell Science*, 2004). Some experts tend to categorise cutaneous forms of LE into three major types; (1) Acute Cutaneous Lupus Erythematosus (ACLE), (2) Subacute Cutaneous Lupus Erythematosus (SCLE), and (3) Chronic Cutaneous Lupus Erythematosus (CCLE). A major form of CCLE is Discoid Lupus Erythematosus (DLE) exists together with many sub-groups of cutaneous LE, such as hypertrophic LE (a form of DLE), Verrucous LE (a form of DLE), Tumid LE, lupus panniculitis, disseminated DLE, Bullous SLE, Telangietactic LE, Chilblain lupus, Childhood DLE, Lupus Erythematosus Profundus and Mucosal DLE. The phrase "cutaneous forms of Lupus Erythematosus" is also meant to encompass cutaneous manifestations of systemic LE. For example in connection with treating cutaneous manifestations in a subject diagnosed with SLE.

Therefore, in interesting embodiments of the present invention the treatment of cutaneous forms of Lupus Erythematosus includes the treatment of Acute Cutaneous Lupus Erythematosus, Subacute Cutaneous Lupus Erythematosus, Chronic Cutaneous Lupus Erythematosus, cutaneous manifestations of Systemic Lupus Erythematosus, and various sub-groups thereof, such as Discoid Lupus Erythematosus, Hypertrophic Lupus Erythematosus, Verrucous Lupus Erythematosus, Tumid Lupus Erythematosus, Lupus Panniculitis, Disseminated Discoid Lupus Erythematosus, Bullous Systemic Lupus Erythematosus, Telangietactic Lupus Erythematosus, Chilblain lupus, Childhood Discoid Lupus Erythematosus, Lupus Erythematosus Profundus and/or Mucosal Discoid Lupus Erythematosus.

The terms "cutaneous manifestations" and "cutaneous presentations" are interchangeable terms, which refer to a pathological or clinical feature present in the skin or in the mucosa of an individual in risk of, suffering from, or diagnosed with a connective tissue disease of the skin.

Typical cutaneous manifestations (either pathologically or clinically) of cutaneous forms of Lupus Erythematosus include the presence of a patchy dermal lymphocytic infiltrates; liquefaction degeneration of the basal cell layer of the epidermis; oedema of the connective tissue below the epidermis; fibrinoid of the connective tissue below the epidermis; atrophy of the dermis; keratotic plugging: thinning and pallor of the epidermis with relative hyperkeratosis and plugging of the follicular mouth; thickening of the basement membrane of the epidermis and sometimes small vessels; premature elastotic degeneration of collagen in light exposed areas.

A typical clinical feature is skin rash, chilblain-like lesions, alopecia in scalp lesions, well-defined erythematous patches which may contain scales, hyperkeratosis, telangiectasia, nodular lesions, non-scarring papulosquamous lesions and annular polycyclic lesions.

The cutaneous manifestations may be limited to the skin, such as the skin of scalp, ears, nose, lips, arms, legs, fingers, feet, toes, breast, and trunk. Furthermore, the cutaneous manifestations may be found in the buccal mucosa, such as lips and tongue and in the mucosa of vulva and anus.

The term "DLE" defines a connective-tissue disease affecting only the skin, most frequently the skin in the face, neck and the scalp. DLE is characterised by well-defined red scaly patches of variable size (coin-shaped red bumps), which heal with atrophy, scarring and pigmentary changes. As DLE lesions heal, they leave thickened, scarred areas of skin. When the scalp is severely affected, there may be associated hair loss (alopecia). DLE is sometimes called chronic cutaneous lupus erythematosus (CCLE).

The term "SCLE" defines a specific subset of lupus and may be characterised as a non-scarring non-atrophy-producing photosensitive dermatosis. SCLE may occur in patients with systemic Lupus Erythematosus (SLE), Sögren syndrome, and in patients with deficiency of the second component of complement (C2d). It may also be drug induced. Some patients also have the lesions of DLE, and some may develop small vessel vasculitis. Therefore, SCLE may be regarded as a cutaneous disease categorised as an intermediate between discoid Lupus Erythematosus and systemic Lupus Erythematosus. SCLE may accompany other diseases or the treatment of such diseases, such as in the course of PUVA treatment of psoriasis, radiation therapy, or in connection with cancer, such as for example Hodgkin's disease, cancers of the lung, breast and liver.

The term "ACLE" defines a "butterfly rash". The butterfly rash has an abrupt onset and can last for hours or days, and usually heals without scarring. Typically, it is localized in the face, but it could occur anywhere on the body. Typically, it is present in patients diagnosed with SLE. Variations of this rash have been observed, including bullous formations or blisters.

Systemic Lupus Erythematosus (SLE) is regarded as a distinct disease from the cutaneous forms of Lupus Erythematosus. Individuals diagnosed with SLE may have cutaneous manifestations, such as cutaneous manifestations typically found in ACLE, SCLE and DLE. Some individuals may suffer from Bullous systemic lupus erythematosus that shows cutaneous manifestations.

Therefore, the phrase "cutaneous manifestations of systemic Lupus Erythematosus" is meant to encompass that some patients diagnosed with Systemic Lupus Erythematosus also have cutaneous disease, such as cutaneous manifestations similar to those found in patients diagnosed with ACLE, SCLE and DLE.

As mentioned, the underlying pharmacodynamic principle of this invention relates to enhancing the activity of $beta_2$ adrenergic receptors in the skin, where such $beta_2$ adrenergic receptors at least are expressed in leukocytes, such as in the T-lymphocyte and wherein the agonistic activity of a $beta_2$ agonist reduces the skin lesions.

Therefore, a $beta_2$ agonist may be used in the treatment of all kinds of skin diseases where the lymphocytic infiltration in the epidermis, dermis, and/or mucosa is a pathological feature of the skin disease.

Therefore, according to this invention another connective tissue disease of the skin may be treated with a $beta_2$ agonist. The term "connective tissue diseases" refer to a heterogeneous group of diseases, some hereditary, others acquired, characterized by abnormal structure or function of one or more of the elements of connective tissue, i.e., collagen, elastin, or the mucopolysaccharides and wherein the skin can be affected. The phrase, "connective tissue diseases of the skin" is meant to define a connective tissue disease that has cutaneous manifestations. Thus, the connective tissue disease may be a systemic disease where the skin is affected or a cutaneous disease mainly or only affecting the skin. Examples of connective tissue diseases of the skin include at least Scleroderma, Morphoea, Pseudoscleroderma, Occupational scleroderma, Graft-versus-host disease, Eosinophilic fasciitis, Connective tissue panniculitis, Systemic Sclerosis; Mixed connective tissue disease; Lichen sclerosus; Sclerederma; Dermatomyositis; Rheumatoid disease; Still's disease; Sjögrens syndrome and Rheumatic fever.

Still other related diseases where lymphocytic infiltrations are a pathological feature of the skin disease are Jessner's lymphocytic infiltration, polymorphic light eruption (PLE), lymphocytic lymphoma, lymphocytoma cutis and Pemphigous erythematosus.

The term "an individual in need thereof" is meant to define a human or an animal, such as a mammal that is in need of treatment of a connective tissue disease of the skin. The term "an individual" refers to an animal, and yet more typically a mammal. The term "Mammal" as used herein refers to any animal classified as a mammal, including humans, domestic and farm animals, zoo, sports, or pet animals, such as dogs, horses, cats, cattle, etc. Preferably, the individual is a human, a cat, a dog or a horse.

According to the invention, any cutaneous form of LE or other connective tissue diseases of the skin that affects both humans and animals can be treated with a $beta_2$ agonist. For example, the treatment, uses and medicaments described herein may be applied in the treatment of Lupoid dermatitis in the dog and Hyperelastosis cutis in the horse.

Beta$_2$-adrenoceptor agonist (Beta$_2$ agonist)

According to the underlying principle of the present invention, any drug agent or pharmacological tool exhibiting the above-mentioned $beta_2$ agonistic-activities may be applied in compositions, methods and uses as defined herein.

The term "beta$_2$-adrenoceptor agonist" or "beta$_2$ agonist" is intended to mean any drug agent or pharmacological tool of inorganic, organic and biological nature with the ability to selectively or partially stimulate/activate beta$_2$-adrenergic receptors. These receptors are G-protein coupled receptors widely distributed in animals and humans and activated by endogenous catecholamines, and which play important roles in regulating cardiac, vascular, pulmonary, and metabolic functions.

The beta$_2$ agonist is preferably an organic molecule.

In one embodiment of the invention, the beta$_2$ agonist of the invention is a selective binding partner or at least a predominant binding partner for a beta$_2$-adrenergic receptor.

In another embodiment of the invention, the beta$_2$ agonist of the invention may also exert binding capacity to other families of receptors, such as $\alpha 1$, $\alpha 2$ $\beta 1$ and $\beta 3$-adrenergic receptors, as long as the agonistic activity towards $\beta_2$-adrenergic receptors is sufficient to obtain the desired effects according to the invention. Thus, the beta$_2$ agonist may exhibit unspecific binding to a beta$_2$-adrenergic receptor.

The beta$_2$-agonistic activity of a drug agent or pharmacological tool towards beta$_2$-adrenergic receptors is easily confirmed by methods known to the person skilled in the art. One example is by testing the agonistic activity in a binding assay using a ligand representing the beta$_2$-adrenergic receptors, such as the binding assay conducted by MDS Pharma Services (Catalogue no. 204110 MDS Pharma Services Discovery, 2004-2005). The agonistic activity is determined by the measure of the concentration (nM) of the beta$_2$ agonist required to produce half maximal effect ($EC_{50}$). The concentration required should in general be less than 10.000 nM as measured by the binding-based assay conducted by MDS Pharma Services or according to a similar binding-based assay. The concentration resulting in $EC_{50}$ is preferably less than 7000 nM, more preferably less than 5000 nm, such as less than 4000, 3000, 2000, 1000, 800, 700, 600, 500, 400, 300, 250, 200, 150, 100, 80, 60, 40, 20 or 10 nM.

According to another alternative, the agonist activity of the beta$_2$ agonist of the invention may be determined by a cell assay described by McCrea and Hill S J. (McCrea and Hill S J. Salmeterol, a long-acting beta$_2$-adrenoceptor agonist mediating cyclic AMP accumulation in a neuronal cell line. *Br J Pharmacol.* 1993; 110:619-26.) In one embodiment of the invention, the beta$_2$ agonist of the invention has a relative potency to a selective agonist, such as formoterol or terbutaline, between 0.01 and 1000, preferably between 0.1 and 500, such as between 1 and 200 when tested in the above-mentioned cell assay of McCrea and Hill S J.

According to still another alternative, the beta$_2$ agonist of the invention has a relative potency to salbutamol of at least 0.01 and up to 1000 with respect to acting as a beta$_2$ agonist in the above-mentioned binding-based assay or cell assay. Preferably, the beta$_2$ agonist has a relative potency to salbutamol ranging between 0.02 and 500, more preferably between 0.1 and 100 when tested in the above-mentioned cell assay of McCrea and Hill S J.

Currently, a number of beta$_2$ agonists are available. Most of them have a structure related to catecholamines. Therefore, in one embodiment of the invention the beta$_2$ agonist is selected from the group of beta$_2$ agonists that comprises, as part of their backbone structure, the following structural formula I:

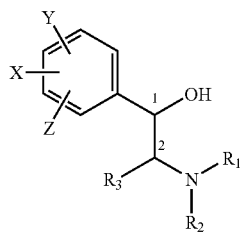

I

The terms, Z, Y and X, are meant to define substituents of the phenyl rings of structural formula I so as to define unsubstituted, mono-substituted, di-substituted or tri-substituted phenyl ring, wherein Z, Y and X may be the same or different.

According to the invention, the terms Z, X, and Y may independently designate radicals selected from hydrido (H), optionally substituted $C_{1-6}$-alkyl, $C_{4-6}$-cycloalkyl, $C_{2-6}$-alkenyl, $C_{2-6}$-alkynyl, $C_{1-6}$-alkoxyl, phenyl, $C_{7-14}$alkaryl, $C_{7-14}$alkheterocyclyl, acyl (OOR'), cyano (CN), urea (NH—CO—NH2), formamide (NH—CO), trihalogenmethyl, halogen (Br, Cl, F, I), hydroxy (OH), hydroxy derivative (OR'), primary amino (NH$_2$), secondary amino (NHR'), tertiary amino (NR'R"), carboxy (CO), carboxy derivative (CO—R'), sulfonyl (HSO$_2$), sulfonyl derivative (R'—SO$_2$,) and sulfonamide (NH—SO$_2$—R'). Furthermore, two of the groups selected from Z, X and Y may together form a 5 or 6 membered carbon ring or a carbon ring with one nitrogen atom (N) in the ring, e.g. where Z and X, Y and X, or Y and Z together forms a 5 or 6 membered carbon ring or a carbon ring with one nitrogen atom in the ring (a hetero ring).

The terms "$R_1$" and "$R_2$" refer to substituents of the amino atom that are attached to carbon atom 2 ($C_2$) of structural formula I. $R_1$ and $R_2$ may independently designate a radical selected from hydrido (H), $C_{1-6}$-alkyl, $C_{4-6}$-cycloalkyl, $C_{2-6}$-alkenyl, $C_{2-6}$-alkynyl, $C_{1-6}$-alkoxyl, $C_{7-14}$ alkaryl, $C_{7-14}$ alkheterocyclyl, and $R_1$ and $R_2$ may together form a 5 or 6 membered carbon ring or a carbon ring with one nitrogen atom (N) in the ring.

The term "$R_3$" represents a radical selected from hydrido (H), halogen (Br, Cl, Fl, I), $C_{1-6}$-alkyl, $C_{4-6}$-cycloalkyl, $C_{2-6}$-alkenyl and $C_{2-6}$-alkynyl.

The terms R' and R" independently define a radical selected from $C_{1-6}$-alkyl, $C_{4-6}$-cycloalkyl, $C_{2-6}$-alkenyl, $C_{2-6}$-alkynyl, $C_{1-6}$-alkoxyl, $C_{7-14}$ alkaryl, $C_{7-14}$ alkheterocyclyl, preferably $C_{1-6}$-alkyl, $C_{4-6}$-cycloalkyl, $C_{2-6}$-alkenyl, $C_{2-6}$-alkynyl and $C_{1-6}$-alkoxyl. The term "$C_{1-6}$-alkyl" is meant to define saturated, straight-chained or branched alkyl radical containing from 1 to 6 carbon atoms, e.g. all alkyl radicals from methyl up to hexyl including all isomers thereof, e.g. iso-butenyl.

The term "$C_{2-6}$-alkenyl" defines unsaturated straight chained or branched alkylene radicals containing from 2 to 6 carbon atoms, e.g. 1- or 2-propenyl, 1-, 2- or 3-butenyl and the like and isomers thereof.

"$C_{2-6}$-alkynyl" defines unsaturated chained or branched alkynyl radicals containing from 2 to 6 carbon atoms, e.g. ethynyl, 1- or 1-propynyl, 1-, 2- or 3-butynyl and the like and isomers thereof.

The term "$C_{1-6}$-alkoxyl" means alkoxy radicals containing up to 6 and preferably up to 4 carbon atoms, e.g. methoxy, ethoxy, propoxy etc.

The term "$C_{4-7}$-cycloalkyl" means a cycloalkane having from 4 to 7 carbon atoms, such as cyclobutane, cyclopentane and cyclohexane.

The term "$C_{7-14}$ alkaryl" embraces aryl-substituted alkyl radicals such as benzyl, diphenylmethyl, phenethyl, and diphenethyl having from 7 to 14 carbon atoms.

The term "$C_{7-14}$ alkheterocyclyl" designates an alkyl substituted heterocyclic group having from 7 to 14 carbon atoms in addition to one or more heteroatoms, N, S, P, or O (e.g. 3-furanylmethyl, 2-furanylmethyl, 3-tetrahydrofuranylmethyl, or 2 tetrahydrofuranylmethyl) Nonlimiting examples of heterocylics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyridinyl, pyridazinyl, pyrimidinyl.

The groups, $C_{1-6}$-alkyl, $C_{4-6}$-cycloalkyl, $C_{2-6}$-alkenyl, $C_{2-6}$-alkynyl, $C_{1-6}$-alkoxyl, $C_{7-14}$ alkaryl, and $C_{7-14}$ alkheterocyclyl may optionally be mono or di-substituted with primary amino (NH$_2$), secondary amino (NHR'), tertiary amino (NR'R"), OH, cyano, nitro and halogen, wherein R' and R" are as defined herein.

The term "halogen" defines bromine, chlorine, fluorine and iodine.

The term "hydrido" designates a single hydrogen atom (H).

In one embodiment, the terms Z, X, and Y may independently designate radicals selected from hydrido (H), optionally substituted $C_{1-6}$-alkyl, $C_{4-6}$-cycloalkyl, $C_{2-6}$-alkenyl, $C_{2-6}$-alkynyl, $C_{1-6}$-alkoxyl, phenyl, $C_{7-14}$ alkaryl, $C_{7-14}$ alkheterocyclyl, (OOR'), cyano (CN), urea (NH—CO—NH2), formamide (NH—CO), trihalogenmethyl, halogen (Br, Cl, F, I), hydroxy (OH), hydroxy derivative (OR'), primary amino (NH$_2$), secondary amino (NHR'), tertiary amino (NR'R"), carboxy (CO), carboxy derivative (CO—R'), sulfonyl (HSO$_2$), sulfonyl derivative (R'—SO$_2$,) and sulfonamide (NH—SO$_2$—R'), wherein R' and R" preferably designates $C_{1-6}$-alkyl, $C_{2-6}$-alkenyl, $C_{2-6}$-alkynyl and $C_{1-6}$-alkoxyl.

In one further preferred embodiment, the phenyl ring of structural formula I defines un-substituted, mono-substituted or di-substituted phenyl ring, wherein Z and Y may be the same or different and X is hydrido (H).

Furthermore, in still further embodiments, the groups, $C_{1-6}$-alkyl, $C_{4-6}$-cycloalkyl, $C_{2-6}$-alkenyl, $C_{2-6}$-alkynyl, $C_{1-6}$-alkoxyl, $C_{7-14}$ alkaryl, and $C_{7-14}$ alkheterocyclyl may optionally be mono-substituted with primary amino ($NH_2$), secondary amino (NHR'), OH, cyano, nitro and halogen, wherein R' and R" are as defined herein, such as preferably wherein R' and R" preferably designates $C_{1-6}$-alkyl, $C_{4-6}$-cycloalkyl, $C_{2-6}$-alkenyl, $C_{2-6}$-alkynyl and $C_{1-6}$-alkoxyl.

The compounds of the present invention may contain one or more asymmetric carbon atom. Therefore, the instant invention may also include the individual diastereomers and enantiomers, which may be prepared or isolated by methods known to those skilled in the art. For example, the carbon atom designated $C_1$ represents an asymmetric carbon atom and compounds of structural formula I may be provided as a racemate or as enantiomerically pure or enantiomerically enriched "R" or "S" forms.

Examples of beta$_2$ agonists with a backbone structure according to structural formula I are:

Amiterol (4-Amino-[[(1-methylpropyl)amino]methyl]benzenemethanol);
Bamethan ((Butylamino)methyl]-4-hydroxybenzenemethanol);
Bitolterol (4-[2-[(1,1-Dimethylethyl)amino]-1-hydroxyethyl]-1,2-phenylene 4-methylbenzoate);
Butaxamine (α-1-[[(1,1-Dimethylethyl)amino]ethyl]-2,5-dimethoxybenzenemethanol);
Carbuterol ([5-[2-[(1,1-Dimethylethyl)amino]-1-hydroxyethyl]-2-hydroxyphenyl]urea);
Clenbuterol (4-Amino-3,5-dichloro-[[(1,1-Dimethylethyl)amino]methyl]-benzenemethanol);
Clorprenaline (2-Chloro-[[(1-methylethyl)amino]methyl]benzenemethanol);
Colterol (4-[2-[(1,1-Dimethylethyl)amino]-1-hydroxyethyl]-1,2-benzenediol);
Deterenol (4-Hydroxy-[[(1-methylethyl)amino]methyl]benzenemethanol);
Dioxethedrin (4-[2-(Ethylamino)-1-hydroxypropyl]-1,2-benzenediol);
Etafedrine ([1-(Ethylmethylamino)ethyl]benzenemethanol);
Ethylnorepinephrine (2-Amino-1-(3,4-dihydroxyphenyl)-1-butanol);
Fenoterol (5-[1-Hydroxy-2-[[2-(4-hydroxyphenyl)-1-methylethyl]amino]ethyl]-1,3-benzenediol);
Flerobuterol (α-[[(1,1-Dimethylethyl)amino]methyl]-2-fluorobenzenemethanol);
Formoterol (N-[2-Hydroxy-5-[1-hydroxy-2-[[2-(4-methoxyphenyl)-1-methylethyl]amino]ethyl]phenyl]formamide);
Hexoprenaline (4,4'-[1,6-Hexanediylbis[imino(1-hydroxy-2,1-ethanediyl)]]bis-1,2-benzenediol);
Indacaterol (5-[2-[(5,6-Diethyl-2,3-dihydro-1H-inden-2-yl)amino]-1-hydroxyethyl]-8-hydroxy-2(1H)-quinolinone);
Isoetarine (4-[1-Hydroxy-2-[(1-methylethyl)amino]butyl]-1,2-benzenediol);
Isoproterenol (Isoprenaline, (4-[1-Hydroxy-2-[(1-methylethyl)amino]ethyl]-1,2-benzenediol); Mabuterol (4-Amino-3-chloro-[(dimethylethylamino)methyl]-5-(trifluoromethyl)benzene methanol);
Medroxalol (5-[2-[[3-(1,3-Benzodioxol-5-yl)-1-methylpropyl]amino]hydroxyethyl]-2-hydroxybenzamide);
Meluadrine (2-Chloro-[[(1,1-dimethylethyl)amino]methyl]-4-hydroxybenzenemethanol);
Nardeterol (α-[[[3-(1H-Benzimidazol-1-yl)-1,1-dimethylpropyl]amino]methyl]-2-fluoro-4-hydroxybenzenemethanol);
2-(Methylamino)-1-phenyl-1-propanol;
Norbudrine (4-[2-(Cyclobutylamino)-1-hydroxyethyl]-1,2-benzenediol);
Norepinephrine (Arterenol,4-(2-Amino-1-hydroxyethyl)-1,2-benzenediol);
Orciprenaline (Metaproterenol, 5-[1-Hydroxy-2-[(1-methylethyl)amino]ethyl]-1,3-benzenediol);
Picumeterol (4-Amino-3,5-dichloro-[[[6-[2-(2pyridinyl)ethoxy]hexyl]amino]methyl]-benzenemethanol);
Pirbuterol (6-[[(1,1-Dimethylethyl)amino]methyl]-3-hydroxy-2,6-pyridinedimethanol);
Procaterol (8-Hydroxy-5-[1-hydroxy-2-[(1-methylethyl)amino]butyl]-2(1H)-quinolinone);
Protokylol (4-[[2-[2-(1,3-Benzodioxol-5-yl)-1-methylethyl]amino]-1-hydroxyethyl]-1,2-benzenediol);
Quinprenaline (8-Hydroxy-[[(1-methylethyl)amino]methyl]-5-quinolinemethanol);
Reproterol (7-[3-[[2-(3,5-Dihydroxyphenyl)-2-hydroxyethyl]amino]propyl]-3,7-dihydro-1,3-dimethyl-1H-purine-2,6-dione);
Rimiterol (4-(Hydroxy-2-piperidinylmethyl)-1,2-benzenediol);
Salbutamol, (Albuterol (1-[[(1,1-Dimethylethyl)amino]methyl]-4-hydroxy-1,3-benzenedimethanol);
Salmefamol (4-Hydroxy-'-[[[2-(4-methoxyphenyl)-1-methylethyl]amino]methyl]-1,3-benzenedimethanol);
Salmeterol (4-Hydroxy-'-[[[6-(4-phenylbutoxy)hexyl]amino]methyl]-1,3-benzenedimethanol);
Soterenol (N-[2-Hydroxy-5-[1-hydroxy-2-[(methylethyl)amino]ethyl]phenyl]-methanesulfonamide);
Sulfonterol (α-[[(1,1-Dimethylethyl)amino]methyl]-4-hydroxy-3-[(methylsulfonyl)methyl]-benzenemethanol);
Terbutaline (5-[2-[(1,1-Dimethylethyl)amino]-1-hydroxyethyl]-1,3-benzenediol);
Tulobuterol (2-Chloro-[(1,1-dimethylethylamino)methyl]benzenemethanol);
Zilpaterol (4,5,6,7-Tetrahydro-7-hydroxy-6-[(1-methylethyl)amino]imidazo[4,5,1-jk][1]benzazepin-2(1H)-one);
Zinterol (N-[5-[2-[(1,1-Dimethyl-2-phenylethyl)amino]-1-hydroxyethyl]-2-hydroxyphenyl]methanesulfonamide).

Therefore, some embodiments of the invention include a beta$_2$ agonists that is a catecholamine derivative selected from the group comprising Amiterol; Bamethan; Bitolterol; Butaxamine; Carbuterol; Cimaterol; Colterol; Clenbuterol; Clorprenaline; Colterol; Deterenol; Dioxethedrin; Etafedrine; Ethylnorepinephrine; Fenoterol; Flerobuterol; Formoterol; Hexoprenaline; Indacaterol; Isoetarine; Isoproterenol (Isoprenaline); Mabuterol; Medroxalol; Meluadrine; Nardeterol; Norbudrine; Norepinephrine (Arterenol); Orciprenaline (Metaproterenol); Picumeterol; Pirbuterol; Procaterol; Protokylol; Quinprenaline; Reproterol; Rimiterol; Salbutamol (Albuterol); Salmefamol; Salmeterol; Soterenol; Sulfonterol; Terbutaline; Tulobuterol; Zilpaterol; Zinterol; a stereoisomer thereof; a physiologically acceptable derivative thereof; a pharmaceutically acceptable salt thereof; and mixtures thereof.

Further examples of beta$_2$ agonists include those, which as part of their backbone have a structure closely related to the above-mentioned structural formula I, but where the asymmetric carbon atom ($C_1$) is missing:

Un-limited examples are:
Broxaterol (3-Bromo-[[(1,1-dimethylethyl)amino]methyl]-5-isoxazolemethanol)
Methoxyphenamine (2-Methoxy-N,-dimethylbenzeneethanamine) and;
Phenisonone (1-(3,4-Dihydroxyphenyl)-2-[(1-methylethyl)amino]-1-propanone).

Further examples of beta₂ agonists also include those having a structure different from structural formula I:
Un-limited examples are:
Tretoquinol (Trimetoquinol, 1,2,3,4-Tetrahydro-1-[(3,4,5-trimethoxyphenyl)methyl]-6,7-isoquinolinediol); and
Sibenadet (4-Hydroxy-7-[2-[[2-[[3-(2-phenylethoxy)propyl] sulfonyl]ethyl]amino]ethyl]-2(3H)-benzothiazolone).

Additionally, a number of beta₂ agonists are presently known according to their Research Code; AR-C68397, CHF-1035, QAB-149 (From Novartis/Skyepharma), GW-685698 (GSK), GW-159797 (GSK), AD-237 (Arakis, Vectura), HOKU-81, 678007 (GSK), 159802 (GSK), 642444 (GSK), 159797 (GSK), 597901 (GSK), KUR-1246, KUL-7211, KUL-1248, AR-C89855, 5-1319 and TA-2005.

Accordingly, a beta₂ agonists of this invention may be selected from the group comprising Amiterol; Bamethan; Bitolterol; Butaxamine; Carbuterol; Cimaterol; Colterol; Clenbuterol; Clorprenaline; Colterol; Deterenol; Dioxethedrin; Etafedrine; Ethyinorepinephrine; Fenoterol; Flerobuterol; Formoterol; Hexoprenaline; Indacaterol; Isoetarine; Isoproterenol (Isoprenaline); Mabuterol; Medroxalol; Meluadrine; Nardeterol; Norbudrine; Norepinephrine (Arterenol); Orciprenaline (Metaproterenol); Picumeterol; Pirbuterol; Procaterol; Protokylol; Quinprenaline; Reproterol; Rimiterol; Salbutamol (Albuterol); Salmefamol; Salmeterol; Soterenol; Sulfonterol; Terbutaline; Tulobuterol; Zilpaterol; Zinterol; Broxaterol; Methoxyphenamine; Phenisonone; Tretoquinol (Trimetoquinol); Sibenadet; AR-C68397; CHF-1035; QAB-149; GW-685698 (GSK); GW-159797 (GSK); AD-237 (Arakis; Vektura); HOKU-81; 678007 (GSK); 159802 (GSK); 642444 (GSK); 159797 (GSK); 597901 (GSK); KUR-1246; KUL-7211; KUL-1248; AR-C89855; S-1319; TA-2005 or a stereoisomer thereof, an enantiomer thereof, a physiologically acceptable derivative thereof, and/or a pharmaceutically acceptable salt thereof.

In interesting embodiments of the invention, the beta₂ agonist has a suitable log P value and a molecular size that are very well suited and adaptable for topical application to skin. Therefore, a beta₂ agonist of this invention preferable has a log P value ranging between −4 to 4, preferable between −3.5 and 3.5, even more preferable between −3 and 3. Optimally, the log P value ranges between −3.5 and 3, such as between −3.5 and 2.5, such as between −3.5 and 2. Furthermore, the molecular weight of a beta₂ agonist od thid invention should be less than 800 Dalton, preferable less than 700, 600 and 500 Dalton. Even more preferable less than 450 Dalton, such as less than 400 Dalton. In still more preferred embodiments, the molecular weight is less than 300 Dalton, such as ranging from about 136 to about 500 Dalton, from about 136 to 450 Dalton, 136 to 400 Dalton. In even more preferred embodiments, the beta₂ agonist has a molecular weight ranging from 136 to about 350 Dalton, such as from 136 to 300 Dalton.

Therefore, in more preferred embodiments, the beta₂ agonist is a catecholamine derivative selected from the group comprising Amiterol; Bamethan; Butaxamine; Carbuterol; Cimaterol; Colterol; Clenbuterol; Clorprenaline; Colterol; Deterenol; Dioxethedrin; Etafedrine; Ethylnorepinephrine; Isoetarine; Isoproterenol (Isoprenaline); Mabuterol; Medroxalol; Meluadrine; Norbudrine; Norepinephrine (Arterenol); Orciprenaline (Metaproterenol); Procaterol; Rimiterol; Salbutamol (Albuterol); Salmefamol; Salmeterol; Soterenol; Sulfonterol; Terbutaline; Tulobuterol; a stereoisomer thereof, an enantiomer thereof, a physiologically acceptable derivative thereof, and/or a pharmaceutically acceptable salt thereof.

In a currently interesting embodiment of the invention, the beta₂ agonist is salbutamol or a physiologically acceptable derivative thereof, and/or a pharmaceutically acceptable salt thereof, e.g. the sulphate or hydrochloride salt of salbutamol, or an amino acid salt of salbutamol, such as a salt of salbutamol and an amino acid.

As mentioned the beta₂ agonists may be provided as the stereoisomer thereof, the enantiomer thereof, the physiologically acceptable derivative thereof, and/or the pharmaceutically acceptable salts thereof.

It will be appreciated by those skilled in the art that the above-mentioned list of beta₂ agonists may be modified at any of the functional groups in the compounds to provide physiologically acceptable derivatives thereof. Of particular interest are derivatives formed by modification of the hydroxyl groups or at the amino groups. It will be appreciated by those skilled in the art that the physiologically acceptable derivatives may be derivatized at more than one position.

By the term "physiologically acceptable derivatives thereof" is meant any physiologically acceptable ester, or salt of such ester, of a beta₂ agonists of the invention which, upon administration to a human or animal, is capable of providing (directly or indirectly) a beta₂ agonists of the invention or an active metabolite or residue thereof. That is to say that the physiologically acceptable derivative thereof is meant to define a prodrug of the beta₂ agonist. Typical examples of suitable esters are formate, acetate, proprionate, and benzoylate.

By the term "pharmaceutically acceptable salts" is meant salts of a beta₂ agonist that are derived from physiologically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Furthermore, salts may be derived from natural amino acids, such as from an essential amino acid.

The beta₂ agonist can be supplied in the form of a pharmaceutically active salt, a prodrug, an isomer, a tautomer, a racemic mixture, or in any other chemical form or combination thereof that, under physiological conditions, still provides agonistic activity towards the beta₂-adrenergic receptor. The present invention includes all possible diastereomers and enantiomers as well as their racemic and resolved, enantiomerically pure forms.

The enantiomeric forms may be of either the (R) or the (S) configuration, or may be a mixture thereof. Thus, the beta₂ agonist according to the invention may be enantiomerically pure, or be stereoisomeric or diastereomeric mixtures.

The term "stereoisomers thereof" encompasses any isomers that possess identical constitution, but which differ in the arrangement of their atoms in space, such as enantiomers, diastereoisomers, and cis-trans isomers.

In interesting embodiments of the invention, wherein the beta₂ agonist has an asymmetric carbon atom, the beta₂ agonist is supplied as an enantiomeric pure or enantiomeric enriched form. The term "enantiomeric enriched form" encompasses mixtures of R and S enantiomers, where either the R or the S enantiomer is quantitatively present in excess of either the S or R enantiomer, respectively. When they are diastereoisomers, it is called diastereoselectivity and is quantitatively expressed by the diastereoisomer excess. The enantiomeric enriched form encompasses mixtures of the two enantiomers, where the ratio of the R enantiomer to the S enantiomer is ranging between 70:30 to 100:0, such as where at least 70% of the mixture is in the form of the R enantiomer, such as at least 75%, 80%, 85%, 90; or 95% is present in the form of the R enantiomer.

It is well known in the art that R and S enantiomers often possess distinctive biological activities. Therefore, in interesting embodiments of the invention, where the $beta_2$ agonist is a catecholamine derivative with one asymmetric carbon atom at $C_1$ of structural formula I, the $beta_2$ agonist is provided in the R-enantiomeric form because the inventor has shown that the topical application of this enantiomer does not cause adverse reactions, such as those reported for the corresponding racemic mixture. Furthermore, the inventor has also proved that this enantiomer is effective in the topical treatment of connective tissue diseases.

Therefore, in presently preferred embodiments of the invention, the $beta_2$ agonist is provided as the enantiomer, which is pharmacologically active in the treatment of connective tissue diseases and which further does not cause sensitization of the skin after topical application to skin. According to this invention, such embodiments include at least enantiomerically pure or enantiomerically enriched R-enantiomer of $beta_2$ agonists comprising in their backbone the spatial R configuration at $C_1$ of structural formula I as depicted above.

Such preferred embodiments of the invention comprises a $beta_2$ agonist according to formula I, wherein the carbon atom $C_1$ of structural formula I designate an asymmetric carbon atom with substituents forming an R-configuration.

Thus, a $beta_2$ agonist of this invention may be provided as the enantiomeric form that has the spatial R-configuration at $C_1$ of structural formula I. Such a $beta_2$ agonist may be enantiomerically pure or enantiomerically enriched R-enantiomer of a $beta_2$ agonist selected from Amiterol; Bamethan; Bitolterol; Butaxamine; Carbuterol; Cimaterol; Colterol; Clenbuterol; Clorprenaline; Colterol; Deterenol; Dioxethedrin; Etafedrine; Ethylnorepinephrine; Fenoterol; Indacaterol; Isoproterenol (Isoprenaline); Mabuterol; Meluadrine; Nardeterol; Norbudrine; Norepinephrine (Arterenol); Orciprenaline (Metaproterenol); Picumeterol; Pirbuterol; Quinprenaline; Reproterol; Salbutamol (Albuterol); Salmeterol; Soterenol; Sulfonterol; Terbutaline; Tulobuterol; Zinterol; a physiologically acceptable derivative thereof and/or a pharmaceutically acceptable salt thereof. In such embodiments $R_3$ of structural formula I designate hydrido only.

In other embodiments, where $R_3$ designates a radical selected from the group consisting of halogen, $C_{1-6}$-alkyl, $C_{4-6}$-cycloalkyl, $C_{2-6}$-alkenyl and $C_{2-6}$-alkynyl, the $beta_2$ agonist may be provided in two diastereomeric forms both having the spatial R-configuration at $C_1$ such as the RR or RS diastereomer of Ethylnorepinephrine, Flerobuterol, Formoterol, Hexoprenaline, Isoetarine, Medroxalol, 2-(Methylamino)-1-phenyl-1-propanol, Procaterol, Protokylol, Rimiterol, Salmefamol and Zilpaterol a physiologically acceptable derivative thereof and/or a pharmaceutically acceptable salt, wherein the R in RS refer to the asymmetric carbon C1 of structural formula I. It should be understood that such diastereomers can be provided as the diastereomeric pure RS or RR isomer or as the diastereomeric enriched RS or RR isomer.

Therefore, the term "R-enantiomers of $beta_2$ agonist" is meant to include any $beta_2$ agonists comprising in their backbone the R-enantiomer configuration of structural formula I, despite the fact that they have an additional chiral centre. Thus, an R-enantiomers of a $beta_2$ agonist encompasses RR and RS enantiomers, where the first mentioned R refer to the chiral centre of the carbon atom C1 of structural formula I, such as Ethylnorepinephrine, Flerobuterol, Formoterol, Hexoprenaline, Isoetarine, Medroxalol, 2-(Methylamino)-1-phenyl-1-propanol, Procaterol, Protokylol, Rimiterol, Salmefamol, Zilpaterol a physiologically acceptable derivative thereof and/or a pharmaceutically acceptable salt.

In a current interesting embodiment of the invention the $beta_2$ agonist is R-salbutamol or a physiologically acceptable derivative thereof, and/or a pharmaceutically acceptable salt thereof, such as the sulphate or hydrochloride salt of R-salbutamol or an amino acid salt of salbutamol, such as a salt of salbutamol with an amino acid. R-salbutamol is also known as levo-salbutamol, R-albuterol or levalbuterol.

Other preferred $beta_2$ agonists are R-terbutaline and RR-Formoterol.

Manner of Administration and Doses

A $beta_2$ agonist of the invention may be administered to an individual through any route of administration resulting in either local presence of the agonist in skin or in mucous or systemic presence of the agonist. Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical routes of administration.

The phrase "local presence of the agonist in skin or mucous" is meant to include topical administration of the $beta_2$ agonists to skin or mucous, such as mucous of the eye, buccal cavity, nasal cavity, or intestinal tract with the presumption that systemic uptake of the $beta_2$ agonists is limited or nil. Thus, it is intended that less than 15% by weight, such as less than 10%, 8%, 5% and 3% by weight, of the topically administered agonist according to the invention may enter the blood stream or be recovered in urine and faeces.

The phrases "systemic presence of the agonist" and "systemic administration" are interchangeable terms and are meant to include any form of administration of the $beta_2$ agonists resulting in the entrance of the agonist into the blood stream. Therefore, the agonist may be administered by the per-oral, transdermal, transmucosal or the parenteral route.

In a currently interesting embodiment of the invention, the $beta_2$ agonist is intended for the local treatment of the skin and is to be administered topically, such as to the skin an individual. The treatment is preferentially accomplished by topical application of a $beta_2$ agonist as defined herein to the affected skin areas for the local treatment of the skin. In such embodiments, the systemic absorption following the topical application should be limited or nil.

The potency of $beta_2$-adrenergic agonists varies significantly for which reason the sufficient clinically relevant dose to be applied as well as the necessary dosage regimen to be applied may vary significantly.

In the case of systemic administration, the daily total dose would typically be in the range of 0.000001-5 mg/(kg body weight) depending on the duration of the treatment, the pharmaceutical formulation of the $beta_2$ agonist and the bioavailability following per-oral administration, transdermal, transmucosal or parenteral administration. The skilled person will appreciate that the total daily dose may be divided into one or more doses, such as two doses per day or three doses per day.

In case of topical administration, the daily dose of the $beta_2$-adrenergic agonist is defined according to the concentration of the $beta_2$-adrenergic agonist in the topically administrable composition. The concentration of the $beta_2$-adrenergic agonist is typically in the range of 0.0001-50.0% (w/w) depending on the duration of the treatment, the type of formulation and the number of times that the topical composition is to be applied daily.

As mentioned in a current interesting embodiment of the invention, the beta$_2$ agonist is R-salbutamol or a pharmaceutically acceptable salt thereof and the effective total daily dose with respect to R-salbutamol to be administered systemically is between 0.05 mg to 10 mg, preferably between 1-2.5 mg. Concerning, topically administrable R-salbutamol or a pharmaceutically acceptable salt thereof, the preferred concentration with respect to R-salbutamol is between 0.01-10.0% (w/w), preferably between 0.05-5.0% (w/w).

In considering administering a beta$_2$ agonist, either as the racemic mixture or as the R-enantiomer, topically to skin, a topically administrable composition should preferably comprise the beta$_2$ agonist in an amount ranging between 0.01 and 10% by weight, preferably between 0.05 and 7% by weight, such as between 0.05 and 6% by weight, 0.05 and 5.5% by weight, 0.05 and 5% by weight, 0.05 and 4.5% by weight, 0.05 and 4% by weight, 0.05 and 3.5% by weight, such as 0.05 and 3% by weight. In still more preferable embodiments of the invention, the dermatological formulation should comprise a beta$_2$ agonist in an amount ranging between 0.2 and 7% by weight, preferably between 0.2 and 6.5% by weight, such as between 0.2 and 6% by weight, 0.2 and 5.5% by weight, 0.2 and 5% by weight, 0.2 and 4.5% by weight, 0.2 and 4% by weight, 0.2 and 3.5% by weight, such as 0.2 and 3% by weight. In further preferable embodiments of the invention, the dermatological formulation should comprise a beta$_2$ agonist in an amount ranging between 0.2 and 2.5% by weight, such as about 0.5%, 1, 1.5, and 2% by weight.

Topically Administrable Compositions

As mentioned, the safe administration of a beta$_2$ agonist may require the administration of an enantiomer or a diastereomer, which does not cause sensitization of skin and still possesses beta$_2$-adrenergic receptor agonistic activity.

Therefore, still another aspect of the invention relates to a dermatological/topical administrable pharmaceutical composition comprising an R enantiomer of a catecholamine derived beta$_2$ agonist, either supplied in the form of the enantiomerically pure enantiomer or as the enriched enantiomer; and which composition further comprises one or more dermatologically acceptable excipients or carriers.

The term "which does not cause sensitization" is meant to define that an enantiomer of a beta$_2$ agonist does not produce contact sensitization of skin or ear swelling when applied in a concentration corresponding to its therapeutically effective concentration, typically between 0.5% and 5% w/w in the contact sensitization test or ear swelling challenge test described by Kalish R et al (Kalish R et al. *Sensitization of mice to topically applied drugs: albuterol, chlorpheniramine, clonidine and nadolol. Contact Dermatitis* 1996 August; 35(2):76-82). Alternatively, test for skin sensitization may be carried out according to the Magnusson and Kligman method (J. Invest. Dermatol. 1969. 52, 268-276) and in accordance with O.E.C.D. Guideline N° 406 of Jul. 17th, 1992, and the test method B.6 of the 96/54 E.E.C Directive.

The phrase "topical administrable pharmaceutical composition" encompasses compositions formulated for application to skin and which are either ready to be applied directly to skin without further dilution or are the result of diluting a concentrate of the beta$_2$ agonist in a physiological acceptable carrier before being applied to skin.

Therefore, the invention provides a topically administrable pharmaceutical composition comprising as the therapeutically active ingredient an enantiomerically pure or an enantiomerically enriched R-enantiomer of a beta$_2$ agonist or a physiologically acceptable derivative thereof or a pharmaceutically acceptable salt thereof, wherein the beta$_2$ agonist is defined according to structural formula II;

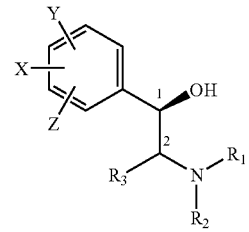

wherein the terms Z, Y, X, $R_1$, $R_2$, $R_3$, R', R" are as defined above with respect to structural formula I; and wherein the composition further comprises one or more dermatologically acceptable excipient or carrier.

Specifically, such a topically administrable composition comprises as the therapeutically active ingredient a beta$_2$-adrenoceptor agonist according to formula II or a physiologically acceptable derivative thereof or a pharmaceutically acceptable salt thereof, wherein the carbon atom at $C_1$ designate an asymmetric carbon having R-configuration and wherein the terms Z, Y, X, $R_1$, $R_2$, $R_3$, R', R" are as defined above.

Such an R-enantiomer (provided as enantiomerically pure or as enantiomerically enriched) is preferably selected from the group consisting of enantiomerically pure or enantiomerically enriched R-enantiomer of Amiterol, Bamethan, Bitolterol, Butaxa mine, Carbuterol, Cimaterol, Colterol, Clenbuterol, Clorprenaline, Colterol, Deterenol, Dioxethedrin, Etafedrine, Ethylnorepinephrine, Fenoterol, Indacaterol, Isoproterenol, Mabuterol, Meluadrine, Nardeterol, Norbudrine, Norepinephrine, Orciprenaline, Picumeterol, Pirbuterol, Quinprenaline, Reproterol, Salbutamol, Salmeterol, Soterenol, Sulfonterol, Terbutaline, Tulobuterol, Zinterol, physiologically acceptable derivatives thereof, and pharmaceutically acceptable salts thereof.

Where the beta$_2$ agonist of structural formula II has more than one asymmetric carbon, such as two symmetric carbon atoms, the beta$_2$ agonist may be provided as the diastereomer where the asymmetric carbon at $C_1$ of structural formula II has the R-configuration. Such beta$_2$ agonists may be selected from Flerobuterol, Formoterol, Hexoprenaline, Isoetarine, Medroxalol, Procaterol, Protokylol, Rimiterol, Salmefamol, Zilpaterol physiologically acceptable derivatives thereof, and pharmaceutically acceptable salts thereof.

In still other embodiments, the topically administrable composition comprises as the beta$_2$ agonist the RR or RS diastereomeric form of beta$_2$ agonists selected from Flerobuterol, Formoterol, Hexoprenaline, Isoetarine, Medroxalol, Procaterol, Protokylol, Rimiterol, Salmefamol, Zilpaterol, a physiologically acceptable derivative thereof, and a pharmaceutically acceptable salt thereof.

As mentioned, the present inventor has shown that the R-enantiomer of Salbutamol does not confer skin sensitization to skin following topical application. Therefore, in a currently interesting embodiment of the invention, the topical composition comprises R-salbutamol or another closely related beta$_2$ agonist, which also has the R configuration at carbon atom $C_1$ of structural formula I.

In a currently interesting embodiment, the topically administrable composition comprises:
i) R-salbutamol, a physiologically acceptable derivative thereof or a pharmaceutically acceptable salt thereof; and
ii) one or more dermatologically acceptable excipients or carriers.

The salt is preferably in the form of the sulphate or hydrochloride salt of R-salbutamol or an amino acid salt of salbutamol, such as a salt of salbutamol with an essential amino acid.

The skilled person will appreciate that topically administrable compositions of the invention may be in any form suitable for being topically applied to skin and with the intention to avoid or at least minimise systemic absorption of the beta$_2$ agonist.

Accordingly, the composition may be in the form of an emulsion such as a cream or a lotion, a gel, a solution, a liniment, an ointment, pasta, a spray, an aerosol, a foam, a liquid or a powder, preferably formulated in a manner that limits the systemic uptake, e.g. such that less than 15% by weight, such as less than 10%, 8%, 5% and 3% by weight, of the topically administered agonist of the invention enters the blood stream following topical administration to the skin or is recovered in urine and faeces.

In other embodiments of the invention, a systemic uptake is tolerable. Therefore, transdermal formulations may also refer to a dermatological composition of the invention.

The concentration of the beta$_2$ agonist may vary significantly depending on its potency. The concentration in the compositions would typically be in the range of 0.0001-50.0% (w/w) depending on the duration of the treatment, the type of formulation and the number of times that the topical composition is to be applied daily. More preferable, the concentration is in the range of 0.01 and 10% by weight, such as more typically 0.02% and 5%. Even more preferably the concentration is between 0.05 and 5% by weight, 0.05 and 4.5% by weight, 0.05 and 4% by weight, 0.05 and 3.5% by weight, such as 0.05 and 3% by weight. In still more preferably embodiments of the invention, the dermatological formulation should comprise a beta$_2$ agonist in an amount ranging between 0.2 and 7% by weight, preferably between 0.2 and 6.5% by weight, such as between 0.2 and 6% by weight, 0.2 and 5.5% by weight, 0.2 and 5% by weight, 0.2 and 4.5% by weight, 0.2 and 4% by weight, 0.2 and 3.5% by weight, such as 0.2 and 3% by weight. In still more preferable embodiments of the invention, the dermatological formulation should comprise a beta$_2$ agonist in an amount ranging between 0.2 and 2.5% by weight, such as about 0.5%, 1, 1.5, and 2% by weight.

Where the topically administrable composition comprises R-salbutamol or a physiologically acceptable derivative thereof or a pharmaceutically acceptable salt thereof, the preferred concentration with respect to R-salbutamol is between 0.01 and 5.0% (w/w), preferably between 0.05 and 2.0% (w/w). In view of the good tolerability of R-salbutamol, the composition to be administered may contain even higher amounts, such as up to 10 and 20% by weight, e.g. between 0.01% and 10% by weight of the composition.

The pharmaceutical compositions of the invention may be formulated in any solid, semi-solid or fluid form suitable for being administered topically according to conventional pharmaceutical practice, see, e.g., "Remington: The science and practice of pharmacy" 20th ed. Mack Publishing, Easton Pa., 2000 ISBN 0-912734-04-3 and "Encyclopaedia of Pharmaceutical Technology", edited by Swarbrick, J. & J. C. Boylan, Marcel Dekker, Inc., New York, 1988 ISBN 0-8247-2800-9.

Generally speaking, dermatological compositions may be provided in several designs such as in the form of an emulsion (including a microemulsion and a liposome formulation), gel, solution, liniment, ointment, foam, spray, aerosol, microsponge, patch or powder.

In one embodiment, the topical administrable composition is a cream. Creams are typically oil-in-water emulsions that contain more than 30% of hydrophilic phase, such as water or aqueous buffers.

A typical dermatological formulation for use in the present invention may be provided in the form of an emulsion, such as oil-in-water emulsion consisting of: an R-enantiomer of a beta$_2$ agonist according to this invention in an amount ranging between 0.01% and 20% by weight and the following dermatologically acceptable ingredients: a fatty component in an amount ranging between 2 and 30% by weight of the composition; an oily component in an amount ranging between 2 and 30% by weight of the composition; water in an amount ranging between 30% and 90% by weight of the composition; an emulsifier in an amount ranging between 0.2 and 10% by weight of the composition; an emollient in an amount ranging between 1 and 20% by weight of the composition; optionally a lipophilic solvent in an amount ranging between 1 and 20% by weight of the composition; optionally a hydrophilic solvent in an amount ranging between 1 and 20% by weight of the composition; optionally a thickener in an amount ranging between 0.2 and 10% by weight of the composition; optionally a co-emulsifier in an amount ranging between 0.2 and 10% by weight of the composition; optionally a preservative in an amount ranging between 0.05 and 3% by weight of the composition; optionally an antioxidant in an amount ranging between 0.05 and 3% by weight of the composition; optionally a pH adjuster in an amount ranging between 0.05 and 3% by weight of the composition; optionally a chelating agent in an amount ranging between 0.05 and 3% by weight of the composition, with the proviso that all constituents make up 100% by weight of the composition.

According to another embodiment, the composition is formulated as an ointment. Ointments are typically water-in-oil emulsions that contain up to 70%, but preferably from approximately 20% to approximately 50%, water or aqueous phases. Hydrocarbons are especially suitable as fatty phase; e.g. vaseline, paraffin oil and/or hard paraffins, which preferably contain suitable hydroxy compounds, such as fatty alcohols or esters thereof, for example cetyl alcohol or wool wax alcohol or wool wax, in order to improve their capacity to bind water. Emulsifiers are corresponding lipophilic substances, such as sorbitan fatty acid esters (Spans), for example sorbitan oleate and/or sorbitan isostearate. Additives to the aqueous phase are, inter alia, moisture-retaining agents, such as polyalcohols, for example glycerol, propylene glycol, sorbitol and/or polyethylene glycol, and preservatives, perfumes, etc.

According to another embodiment, the composition is formulated as an fatty ointment which are anhydrous and contain as base material especially hydrocarbons, for example paraffin, vaseline and/or liquid paraffins, and natural or partially synthetic fats, for example coconut fatty acid triglyceride, or preferably hardened oils, for example hydrogenated groundnut or castor oil, and fatty acid partial esters of glycerol, for example glycerol mono- or di-stearate, and also, for example, the fatty alcohols that increase the water absorption capacity and the emulsifiers and/or additives mentioned in connection with the ointments.

According to another embodiment, the composition is formulated as paste, which is a cream and ointment with secretion-absorbing powder constituents, such as metal oxides, for example titanium oxide or zinc oxide, also talc and/or aluminium silicates, the function of which is to bind any moisture or secretions present.

According to another embodiment, the composition is formulated as a gel. In the case of gels, a distinction is made between aqueous and anhydrous or low-water-content gels which consist of swellable, gel-forming materials. Especially transparent hydrogels based on inorganic or organic macromolecules are used. High molecular weight inorganic components having gel-forming properties are predominantly water-containing silicates, such as aluminium silicates, for example betonite, magnesium aluminium silicate, for example veegum, or colloidal silica, for example aerosil. As high molecular weight organic substances, e.g. natural, semi-synthetic or synthetic macromolecules are used. Natural and semi-synthetic polymers are derived from, e.g. polysaccharides having very varied carbohydrate building blocks, such as celluloses, starches, tragacanth, gum arabic, agar-agar, gelatine, alginic acid and salts thereof, for example sodium alginate, and derivatives thereof, such as lower alkylcelluloses, for example methyl- or ethyl-celluloses, and carboxy- or hydroxy lower alkylcelluloses, for example carboxymethyl- or hydroxyethyl-celluloses. The building blocks of synthetic, gel-forming macromolecules are, e.g. corresponding substituted unsaturated aliphatic compounds, such as vinyl alcohol, vinylpyrrolidine, acrylic acid or methacrylic acid. Examples of such polymers are polyvinyl alcohol derivatives, such as polyviol, polyvinylpyrrolidines, such as collidine, polyacrylates and polymethacrylates, such as Rohagit S or Eudispert. Customary additives, such as preservatives or perfumes, may be added to the gels.

According to another embodiment, the composition is formulated as a foam. Foams are administered, e.g. from pressurised containers and are oil-in-water emulsions in aerosol form, there being used as propellants halogenated hydrocarbons, such as chlorofluoro-lower alkanes, e.g. dichlorodifluoromethane or dichlorotetrafluoroethane. As oily phase e.g. hydrocarbons, such as paraffin oil, fatty alcohols, for example cetyl alcohol, fatty acid esters, such as isopropylmyristate, and/or other waxes are used. As emulsifiers, the following mixtures are used: e.g. mixtures of those having predominantly hydrophilic properties, such as polyoxyethylene sorbitan fatty acid esters (Tweens), and those having predominantly lipophilic properties, such as sorbitan fatty acid esters (Spans). The customary additives, such as preservatives, etc. are added thereto.

Typically, a dermatologically acceptable ingredient to be used in the various formulations can be selected from the following ingredients:

Oily components, which are constituents of the hydrophobic phase of the various dermatological compositions forms and which may be made of one of the following dermatologically acceptable ingredients or a mixture of two or more thereof: almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and teaseed oil), mineral oils, fatty oils, liquid paraffin, mineral oil, isopropyl myristate, beewax, cottonseed oil, cetostearyl alcohol (including mixtures of cetostearyl alcohol and sodium laurilsulfate), lanolin, white soft paraffin, yellow soft paraffin, canola oil, cetyl alcohol (cetanol), peanut oil, oleic acid, isopropyl palmitate, castor oil, stearyl alcohol, jojoba oil, stearic acid and silicone oils.

Fatty components which are constituents of the hydrophobic phase of the various dermatological compositions forms and may be used in combination with or instead of the oil phase and typically includes one or more ingredients selected from beeswax, paraffin, petrolatum, triglycerides, cetyl palmitate, vegetable oils, sorbitan esters of fatty acids (Span), solid macrogols (polyethylene glycols), and condensation products between sorbitan esters of fatty acids and ethylene oxide, e.g. polyoxyethylene sorbitan monooleate (Tween). Typical fatty components may be selected from the group comprising petrolatum, paraffins, vegetable oils, animal fats, synthetic glycerides, waxes, lanolin, and liquid polyalkylsiloxanes. Typical fatty components are but not limited to solid macrogols (polyethylene glycols).

Aaueous phase, which constitutes the hydrophilic phase and which mainly comprise water, hydrophilic solvents, surfactants, emulsifier, preservatives, pH adjusters, flavours, colours and other hydrophilic ingredients.

Hydrophilic solvents which may be added to the aqueous phase, such as polar solvents in the form of water, propylene glycol, glycerol, sorbitol, ethanol, industrial methylated spirit, polyethylene glycols, propylene glycols, propylene carbonate, and triacetin.

Lipophilic solvents, such as non polar solvents in the form of isopropyl alcohol and medium chain triglycerides (MCT) which may be added to the lipophilic phase.

Emollients, such as fatty acid mono, di or tri glycerides, and fatty acid esters, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof and mixtures thereof.

Emulsifiers (emulsifying agents), which may be added either to the aqueous phase or to the oil phase: Compositions of the present invention can include one or more emulsifiers to emulsify the composition. As used herein, the term "emulsifier" means an amphiphilic molecule possessing both polar and non-polar regions which are covalently bound and capable of reducing the surface tension of water and for the interfacial tension between water and an immiscible liquid. The term is meant to include soaps, detergents, emulsifiers, surface active agents, and the like. The emulsifier can be cationic, anionic, non-ionic, or amphoteric. This includes a wide variety of conventional emulsifiers;

Non-ionic Emulsifiers. Examples of non-ionic emulsifiers include, but are not limited to, Polyol esters including glycols (e.g. ethylene glycol, diethylene glycol, glycol stearate and propylene glycol monoesters of fatty acids (propylene glycol stearate, propylene glycol oleate or propylene glycol palmitostearate)) and glycerol esters (e.g. glyceryl stearate, glyceryl monooleate, glyceryl-monolaurate, glyceryl ricinolate, glyceryl monocaprylate);

Sorbitan derivatives, that consists of esters of cyclic anhydrides of sorbitol with a fatty acid (C12-C18). Sorbitan derivatives are divided into two groups i) sorbitan esters of fatty acids (e.g. sorbitan monolaurate, sorbitan monooleate, sorbitan monostearate (SPAN 60™), sorbitan monopalmitate, sorbitan sesquioleate, sorbitan trioleate or sorbitan tristearate) and ii) polyoxyethylene sorbitan esters (e.g. polyoxyethylene sorbitan monostearate (TWEEN 60 ™), polyoxyethylene sorbitan tristearate (TWEEN 65™), polyoxyethlene sorbitan monooleate (TWEEN 80™);

Polyoxyethylene esters (also called macrogol esters) are mixtures of mono- or di-fatty acids esters (from C12 to C18) of polyoxyethylene glycol (PEG), e.g. stearate esters of PEG (PEG-40, PEG-50 and PEG-55), laurate, oleate, and myristate esters of PEG;

Polyoxyethylene ethers are ethers of macrogol and fatty alcohols, such as ethers of the alcohols: stearyl (steareth emulsifiers), cetostearyl (including mixtures of cetosteraryl alcohol and sodium laurilsulfate, ceteareth emulsifiers) and oleyl (oleth emulsifiers);

Poloxamers that are polyoxyethylene-polyoxypropylene derivatives with polyoxyethylene groups (e.g. poloxamers-188);

Nonylphenyl ethers (nonoxinols) that are ethoxylated nonylphenols;

Propylene glycol Diacetate;

Polyvinyl alcohol;

Alkanolamides prepared from reaction of fatty acids with mono or diethanolamine;

Fatty alcohols (e.g. cetyl alcohol and stearate alcohol); alkyl glucosides;

alkyl polyglucosides; polyhydroxy fatty acid amides;

sucrose esters;

fatty acid alkanolamides;

ethoxylated fatty acids;

ethoxylated aliphatic acids;

ethoxylated fatty alcohols (e.g., octyl phenoxy polyethoxyethanoal available under the trade name TRITON X-100 and nonyl phenoxy poly(ethyleneoxy) ethanol available under the trade name NONIDET P-40, both from Sigma, St. Louis, Mo.);

ethoxylated and/or propoxylated aliphatic alcohols;

ethoxylated glycerides;

ethoxylated propoxylated block copolymers such as PLURONIC and TETRONIC surfactants available from BASF.

Cationic Emulsifiers. Examples of cationic emulsifiers include, but are not limited to: salts of primary, secondary, or tertiary fatty amines that optionally may be polyoxyalkylenated; quaternary ammonium salts, such as tetraalkylammonium, alkylamidoalkyltrialkylammonium, trialkylbenzylammonium, trialkylhydroxyalkylammonium, or alkylpyridinium halides (preferably chlorides or bromides) as well as other anionic counter-ions, such as but not limited to, alkyl sulfates, such as but not limited to, methosulfate and ethosulfate; imidazoline derivatives; amine oxides of a cationic nature (e.g., at an acidic pH). Examples of amineoxide emulsifiers include those which are lauryidimethylamine oxide, laurylamidopropyldimethylamine oxide, and cetyl amine oxide.

Anionic Emulsifiers. Examples of anionic emulsifiers include, but are not limited to, sarcosinates, glutamates, alkyl sulfates, sodium or potassium alkyleth sulfates, ammonium alkyleth sulfates, ammonium laureth-n-sulfates, laweth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic emulsifiers may have a metal or organic ammonium counterion.

Amphoteric Emulsifiers. Emulsifiers of the amphoteric type include emulsifiers having tertiary amine groups, which may be protonated, as well as quaternary amine containing zwitterionic emulsifiers. Examples of such amphoteric emulsifiers include, but are not limited to: certain betaines such as cocobetaine and cocamidopropyl betaine; monoacetates such as sodium lauroamphoacetate; diacetates such as disodium lauroamphoacetate; amino- and alkylamino-propionates such as lauraminopropionic acid. Ammoniurn Sulfonate Amphoterics. This class of amphoteric emulsifiers refers to "sultaines" or "sulfobetaines", such as cocamidopropyl-hydroxysultaine.

Preferred emulsifiers are those that have an HLB (i.e., hydrophilic to lipophilic balance) of at least 4 and more preferably at least 6. Even more preferred emulsifiers are hydrophilic emulsifiers having an HLB in the range between 8 and 20, such as in the range between 10 and 20. Most preferred emulsifiers have an HLB of at least 12, such as at least 15. One or more emulsifiers may be used in the compositions of the present invention at a suitable level to produce the desired result. In a preferred embodiment, the one or more emulsifier are present in a total amount of at least 0.1 wt %, more preferably at least 0.5 wt %, and even more preferably at least 1.0 wt %, based on the total weight of the ready to use composition. In order to avoid irritation caused by an emulsifier, in a preferred embodiment the emulsifier is present in a total amount of no greater than 10 wt %, more preferably no greater than 5 wt %, even more preferably no greater than 3 wt %, and even more preferably no greater than 2 wt %, based on the total weight of the ready to use composition.

Polymeric thickeners which may be added to the hydrophilic phase; e.g. gums such as acacia, alginates, carageenan, chitosan, collagen, tragacanth and xantham; celluloses, such as sodium carboxymethyl-, hydroxymethyl-, hydroxypropyl- and hydroxypropylmethyl celluloses; acrylic acids, such as carbomers and polycarbophil; colloidal solids such as silica, clays and microcrystalline cellulose; hydrogels such as polyvinyl alcohol and polyvinylpyrrolidone; thermoreversible polymers such as poloxamers.

pH adjuster (buffering agents) which may be added to the hydrophilic phase, such as diethanolamine, lactic acid, monoethanolamine, triethanolamine, sodium hydroxide, sodium phosphate, citric acid, acetic acid, tartaric acid, hydrogen phosphoric acid, phosphate salts and diethylamine.

Permeation enhancers which may be added either to the hydrophilic or lipophilic phase in order to increase the penetration of Oxaprozin within stratum corneum.

Preservatives, such as antimicrobial agents like benzalkoniumchloride, benzyl alcohol, chlorhexidine, imidazolidinyl urea, phenol, potassium sorbate, benzoic acid, bronopol, chlorocresol, parabens esters, phenoxyethanol and sorbic acid and mixtures thereof.

Humectants may be selected from glycerin, propylene glycol, sorbitol, lactic acid, urea, and mixtures thereof.

Chelating agents, such as citric acid and edetic acid.

Antioxidants, such as alfa-tocopherol, ascorbic acid, ascorbyl palmitate, butylated hydroxyanisole, butylated hydroxytoluene, cysteinesodium ascorbate, sodium metabisulphite Suspending agents that may be selected from the group comprising celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Gel-forming agents (Thickener). Suitable gel bases and viscosity-increasing components (thickeners) may be selected from the group comprising liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch, or cellulose derivatives such as, e.g., carboxymethylcellulose, hydroxyethylcellulose and other cellulose derivatives, water-swellable hydrocolloids, carrageenans, hyaluronates (e.g. hyaluronate gel optionally containing sodium chloride), and alginates including propylene glycol alginate. Further examples are high molecular weight polysaccharide gum, such as xanthan gum.

Thus, in topically administrable compositions of the invention, the beta$_2$ agonist will usually be distributed in a liquid carrier system such as water or any aqueous solution containing organic or inorganic materials. Additionally, the compositions may contain one or more ingredients to modify or enhance their texture, appearance, scent performance or stability. Illustrative additives to the compositions include: oily components, fatty components, ointment bases, hydrophilic solvents, lipophilic solvents, emollients, water, buffering agents, pH-adjusting agents, preservatives, humectants, chelating agents, antioxidants, stabilizers, emulsifying agents, suspending agents, gel-forming agents, perfumes, skin protective agents, fragrances, antiseptics and preservatives.

Topical administrable compositions of the invention are physically and chemically stable. Where phase-separation of the lipophilic and hydrophilic phase of an emulsion is a problem, it has been found important to select an emulsifier that is less sensitive to electrolytes. Therefore, in certain preferred embodiments of the invention, non-ionic emulsifiers shall be selected as the emulsifier. Exemplary non-ionic emulsifiers include, but are not limited to polyol esters including glycols and glycerol esters; sorbitan derivatives including sorbitan esters of fatty acids and polyoxyethylene sorbitan esters; polyoxyethylene esters; polyoxyethylene ethers; poloxamers; nonylphenyl ethers. The preferred ones are sorbitan esters of fatty acids and polyoxyethylene sorbitan esters.

The physical stability can be recognised by observing the tendency of phase separation of the emulsion after challenging the emulsion to physical stress. For example, the emulsion can be exposed to repeating cycles of "freeze and thaw", for example 6 times, followed by centrifugation. Alternatively, the phase separation can be observed after prolonged storage of the emulsion at either 25° C., 40° C., or 60° C. for 1 month, 3 months, 6 months, 12 months, optionally after centrifugation of the dermatological composition. In a certain embodiment of the invention, the dermatological composition is an-oil-in-water emulsion, e.g. provided as a cream or liniment. The ratio between the hydrophilic and lipophilic phase may be adapted in a manner so as to modify the diffusion/solubility of the beta$_2$ agonist within stratum corneum.

The dermatologically administrable pharmaceutical preparations are prepared in a manner known per se by mixing with pharmaceutical adjuncts that are customary for that purpose, for example by dissolving or suspending the active ingredient in the base material or in a portion thereof, if necessary. In order to prepare emulsions in which the active ingredient is dissolved in one of the liquid phases, the active ingredient is, as a rule, dissolved therein before the emulsification; in order to prepare suspensions in which the active ingredient is suspended in the emulsion, the active ingredient is mixed with a portion of the base material after the emulsification and then added to the remainder of the formulation.

Further Ingredients

Further ingredients, either therapeutically active ingredients or dermatologically acceptable ingredients can be co-administered together with the beta$_2$ agonist or added to a medicament or dermatological composition of the invention in order to strengthen, improve, potentiate, or prolong the therapeutic action demonstrated herein or to provide a less toxic, safer, more convenient, better tolerated, or less expensive treatment approach.

Therefore, in some embodiments of the invention, the medicament, methods, uses and dermatological compositions further comprise one or more additional therapeutically active ingredient(s). For example therapeutically active ingredients generally applied in the treatment of connective tissue diseases of the skin, such as NSAID's, and immunosuppressive agents.

However, in preferred embodiments of the invention, the beta$_2$ agonist may be the sole therapeutically active ingredient or the primary/first therapeutically active ingredient administered or present in a medicament because of safety concerns. Likewise, dermatological compositions of the invention preferably comprise as the sole therapeutically active ingredient, or as the primary therapeutically active ingredient, a beta$_2$ agonist as defined herein.

Where it is desirable to add additional therapeutically active ingredients, one or more of the following agents may be excluded from or not applied in substantial amounts in uses, methods, medicaments and dermatological compositions of the invention, because of safety concerns:

An antihistamine or an analogue thereof, for example those disclosed in the patent application US2005192261.

A corticosteroid, e.g. as disclosed in the patent application US2005192261.

Ibudilast and related compounds as defined by structural formula I in the patent application WO05051293. (Co-administration with a corticosteroid or a glucocorticoid receptor modulator)

Selective serotonin reuptake inhibitors (SSRI), e.g. as those disclosed in the patent application US2004220153.

Non-steroidal immunophilin-dependent immunosuppressant (NsIDI) or an NsIDI enhancer (NsIDIE), e.g. as disclosed in the patent application US2004224876.

A steroid, e.g. a steroid as disclosed in the patent application WO2003092617.

Thus, in one embodiment of the invention, a medicament or a topically administrable composition of the invention does not contain substantial amounts of a steroid, such as a corticosteroid. In still further embodiments, the composition does not comprise Ibudilast or a related compound; a selective serotonin reuptake inhibitor (SSRI); a non-steroidal immunophilin-dependent immunosuppressant (NsIDI) and/or an aminosugar.

In another embodiment of the invention, a medicament or a topically administrable composition of the invention does not contain substantial amounts of an anti-histamine; Ibudilast or a related compound; a selective serotonin reuptake inhibitor (SSRI); a non-steroidal immunophilin-dependent immunosuppressant (NSIDI) and/or an aminosugar.

Likewise, these methods of treating exclude co-administration of substantial amounts of one or more or all of the following drug agents; a steroid; Ibudilast or a related compound; a selective serotonin reuptake inhibitor (SSRI); a non-steroidal immunophilin-dependent immunosuppressant (NsIDI) and an aminosugar, or exclude the co-administration of an anti-histamine; Ibudilast or a related compound; a selective serotonin reuptake inhibitor (SSRI); a non-steroidal immunophilin-dependent immunosuppressant (NsIDI) or an aminosugar.

The term "does not contain a substantial amount" is meant to define that the amount does not add any contribution to the treatment of a connective skin disease according to this invention. Typically, such amounts are less than 5%, such as less than 1% or even more preferable less than 0.1% by weight. In even more preferable embodiments, the amount is nil meaning that the above-mentioned compounds are excluded from compositions, methods and uses described herein.

The term "steroid" or "corticosteroid" is meant to define any naturally occurring or synthetic compound characterized by a hydrogenated cyclopentanoperhydrophenanthrene ring system. Naturally occurring corticosteroids are generally produced by the adrenal cortex. Synthetic corticosteroids may be halogenated. Examples of corticosteroids are prednisolone, cortisone, dexamethasone, hydrocortisone, methylprednisolone, fluticasone, prednisone, triamcinolone, and Diflorasone.

The term "Ibudilast or a related compound" is meant to define Ibudilast or a derivative of a pyrazolopyridine as defined in the patent application WO 2005/051293:

The term "selective serotonin reuptake inhibitor (SSRI)" is meant to define any member of the class of compounds that (i) inhibit the uptake of serotonin by neurons of the central nervous system, (ii) have an inhibition constant (Ki) of 10 nM or less, and (iii) a selectivity for serotonin over norepinephrine (i.e., the ratio of Ki(norepinephrine) over Ki(serotonin)) of greater than 100. Typically, SSRIs are administered in dosages of greater than 10 mg per day when used as antidepressants. Examples of SSRIs for use in the invention are fluoxetine, fluvoxamine, paroxetine, sertraline, citalopram, and venlafaxine.

The term "non-steroidal immunophilin-dependent immunosuppressant or (NsIDI)" includes any non-steroidal agent that decreases proinflammatory cytokine production or secretion, binds an immunophilin, or causes a down regulation of the proinflammatory reaction. NsIDIs include calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which binds to an FK506-binding protein, FKBP-12, and block antigen-induced proliferation of white blood cells and cytokine secretion.

The term "anti-histamine" defines a compound that blocks the action of histamine. Classes of antihistamines include, but are not limited to, ethanolamines, ethylenediamine, phenothiazine, alkylamines, piperazines, and piperidines. Examples of Anti-histamines are bromodiphenhydramine, clemizole, cyproheptadine, desloratadine, loratadine, thiethylperazine maleate, and promethazine.

Furthermore, one or more of the following agents may be excluded from co-administration with the beta$_2$ agonist or to be included in a medicament or a dermatological composition of the invention:

- 1,3-bis-(substituted-phenyl)-2-propen-1-ones as disclosed in the patent application US2003236298, e.g. 1,3-bis-(substituted-phenyl)-2-propen-1-ones that has at least one phenyl substituent that is an aryl, heteroaryl or heterocyclic moiety.
- An aminosugar as disclosed in the patent applications US2005130935 or WO 2003097073, such as an aminosugar selected from the group consisting of glucosamine, galactosamine, mannosamine, derivatives and salts thereof, e.g. wherein the aminosugar is N-acetylglucosamine, N-acetylgalactosamine or N-acetylmannosamine is excluded from uses, methods and compositions of the invention.
- pyridazine derivatives as described in US20050176714 or WO2003104204

The term "1,3-bis-(substituted-phenyl)-2-propen-1-ones" refers to those compounds defined by the general formula (1) in the patent application US2003236298, e.g. 1,3-bis-(substituted-phenyl)-2-propen-1-ones that has at least one phenyl substituent that is an aryl, a heteroaryl or s heterocyclic moiety.

The term an "aminosugar" is meant to include those defined in the patent applications, US2005130935 and WO2003097073, such as to encompass one or more amino derivatives of a monosaccharide (aldoses and ketoses) and its corresponding sugar alcohols (alditols) such as trioses, tetroses, pentoses, hexoses, heptoses and octoses. The aldose, ketose, or alditol has one or more hydroxy groups replaced by any amino group at any position, including the anomeric position. An aminosugar is thus a deoxyamino derivative of an aldose, ketose, or alditol. The term is also intended to mean polyamino sugars, wherein more than one hydroxy group has been replaced by an amino group (e.g. dideoxydiamino, trideoxytriamino-derivatives). Moreover, the term "aminosugar" is also intended to mean amino derivatives of di-, oligo- and poly-saccharides comprising at least one of said monosaccharides. Consequently, in the case of di-, oligo- and poly-saccharides, the amino group may be the position of glycosidation.

The term "pyridazine derivative" is meant to include those compounds described by the formula (1) in US20050176714 or WO2003104204. Such pyridazine derivatives are phosphodiesterase IV inhibitors.

Furthermore, one or more of the following agents are undesirable in dermatological compositions: a skin irritant, a cannabinoid or cannabinoid receptor agonist (as disclosed and defined in the patent application WO05102296), an antigen (as disclosed and defined in WO03088997), a scrubbing agent (such as those defined in the patent application JP7304647), a compound of the plant of pepper family (e.g. Piper nigrum L, Piper longum L, Piper angustifolium), (such as compounds defined and disclosed in the patent application JP9110674), a dissolution assistant agent (such as those defined and disclosed in JP 61-154201), an inorganic salt or an organic acid (such as those disclosed and defined in the patent application JP 06-048497), a hypoglycemic agent (such as those disclosed and defined in the U.S. Pat. No. 4,088,756.

EXAMPLES

Example 1

Topically administrable composition of a beta-$_2$ adrenoceptor agonist.

A pharmaceutical composition according to the invention was prepared by dissolving R-salbutamol sulphate in the watery phase prior to mixing the oily phase and watery phase of the following composition (w/w):

| Hydrophobic phase: | |
|---|---|
| Petrolatum | 5.0% |
| Paraffin oil | 10.0% |
| Cetylan (mixture of 9 parts of cetosteraryl alcohol and 1 part of sodium laurilsulfate) | 5.0% |
| Glyceryl monosterate | 6.0% |
| Polyoxyethylene sorbitan monooleate (Tween 80) | 0.5% |
| Hydrophilic phase: | |
| R-Salbutamol sulphate | 0.5% |
| Propylene glycol | 5.0% |
| Benzylalcohol | 0.5% |
| Water: | Ad 100% |

The emulsion was prepared by first dissolving R-salbutamol sulphate in the watery phase, heating the two phases to 70° C. and then mixing the two phases and finally cooling the mixture under agitation.

Examples 2 to 5 concern the treatment of cutaneous manifestation in patients suffering from discoid Lupus Erythematosus or subacute Lupus Erythematosus with the topical composition of Example 1 under the control of a medical doctor of Bispebjerg Hospital, Denmark. The composition was applied to affected areas once or twice per day.

Example 2

A 50 year old woman had been suffering from discoid Lupus Erythematosus for 18 years. Her arms were somewhat affected and the fingers were severely affected with acrocyanosis. During the years, the woman had regularly been treated with strong topical steroids, but with limited effect.

During an aggravation of the disease, which especially affected the fingers, the woman initiated a treatment with the emulsion according to example 1 on the fingers. After 6 weeks of treatment the subject experienced an almost complete recovery and the symptoms of discoid Lupus Erythematosus had virtually gone. The treatment was continued for another 3 months maintaining the fingers free of symptoms.

Example 3

A 59 year old woman had been suffering from discoid Lupus Erythematosus for 6 years. The symptoms started on the chin, but had spread to most of the face. The woman had periodically been treated with strong topical corticosteroids, topical tacrolimus and systemic methotrexate, but without significant improvement of the disease. During an aggravation of the symptoms, the subject initiated a twice daily treatment with the emulsion according to example 1. After 4 weeks of treatment, there was a significant reduction in facial erythema. Newer, smaller patches of erythema disappeared completely after 1 to 2 weeks of treatment.

Example 4

A 66 year old woman had been suffering from discoid Lupus Erythematosus for 32 years. The disease was very severe with a strong affection of the arms and the back and with elements spread to other parts of the body. The woman had been treated with ercoquin and strong topical corticosteroids, but with limited effect.

During an aggravation of the symptoms, the woman initiated a twice daily treatment with the emulsion of example 1. During the first 6 weeks of treatment the subject experienced a significant improvement of larger elements, while small, new elements disappeared completely within days of treatment.

Example 5

An 81 year old woman had been suffering from subacute Lupus Erythematosus for 16 years. The subject was affected on large areas of the body with elements on the back, the breast and the face.

The woman has previously been treated with oral prednisolone, chlorochin, thalidomide and strong topical steroids, but all with limited or no effect.

During an aggravation of the symptoms, the woman initiated a twice daily treatment with the emulsion according to example 1. After 3 weeks of treatment, a significant reduction of all elements was observed. After 7 weeks of treatment, the back was completely free of elements.

Example 6

Assessment of sensitising properties of R-salbutamol. Test for skin sensitization is carried out according to the Magnusson and Kligman method (J. Invest. Dermatol. 1969. 52, 268-276) and in accordance with O.E.C.D. Guideline N° 406 of Jul. 17th, 1992, and the test method B.6 of the 96/54 E.E.C Directive.

Procedure:

The test item (R-salbutamol as the sulphate salt) was diluted with distilled water to prepare a concentration of 0.5% (w/v).

Albino guinea pigs of Dunkin-Hartley strain were exposed to the test item after an acclimatisation period of at least five days.

The Maximum Non Necrotizing Concentration (M.N.N.C.) was determined by injecting by intradermal route the following concentrations of the test item 0.25%, 0.125%, 0.0625%, 0.0312% and 0.0156% diluted in physiological saline solution.

Pre-Maximum Non Irritant Concentration (pre-M.N.I.C.) was determined by application of the test item under an occlusive dressing during 24 hours, at the following concentrations: 0.5%, 0.25%, 0.125% and 0.0625% diluted in physiological saline solution.

Maximum Non Irritant Concentration (M.N.I.C.) was determined by initially establishing an induction phase by intradermal injection with a physiological saline solution and by topical application of distilled water followed by a 18-day rest phase. In the challenge phase where the test item is under occlusive dressing for 24 hours, the test item was applied to the skin of the Albino guinea pigs at the following concentrations: 0.5%, 0.25%, 0.125% and 0.0625% diluted in physiological saline solution. The induction phase was performed by intradermal injection at day 0 the test item at a concentration of 0.5% and by topical application at day 7 of the test item at 0.5% after brushing with a solution of sodium lauryl sulfate.

Results:

No macroscopic cutaneous reactions attributable to allergy was recorded during the examination following the removal of the occlusive dressing (challenge phase) from the treated test animals. No cutaneous intolerance reaction was recorded in animals from the negative control group.

Example 7

The efficacy and safety of a beta$_2$ agonist in the treatment of patients with cutaneous LE can be determined according to a placebo controlled and double blind proof of concept study.

Patients (at least 30 divided in two groups) with clinical diagnosis of either SLE or DLE presenting with a newly developed discoid lesion in the skin are to be enrolled in the study.

Only fresh inflammatory lesions will be examined in the study. Investigators will select one lesion (target lesion) on each patient and examine this particular lesion at each visit. The treated area must not exceed 100 cm$^2$.

There will be two treatment groups: Half of the patients enrolled in the study will treat the selected lesional area with the cream 0.5% of example 1 and half of the patients will treat the selected lesional area with placebo cream. Treatments will be performed twice daily for 8 weeks. Investigator will assess signs and symptoms (Erythema, Scale/Hypertrophy, Dyspigmentation, Scarring/Atrophy/Panniculitis and Induration), measure lesion area and the patient will asses itching and pain (confined to the target lesion) on a visual analogue scale at baseline and after 2, 4, 6 and 8 weeks of treatment.

General improvement (scored by investigator) and patient's assessment of global improvement of the treated lesion will be assessed after 2, 4, 6 and 8 weeks of treatment.

The investigator's assessment of erythema will be performed according to the following score: 0=absent, 1=pink; faint erythema, 2=red, 3=dark red; purple/violaceous/crusted/hemorrhagic.

The investigator's assessment of scale/hypertrophy will be performed according to the following score: 0=absent, 1=scale, 2=verrucous/hypertrophic, The investigator's assessment of dyspigmentation will be performed according to the following score: 0=absent, 1=dyspigmentation.

The investigator's assessment of scarring/atrophy/panniculitis will be performed according to the following score: 0=absent, 1=scarring, 2=severely atrophic scarring or panniculitis.

The investigator's assessment of induration will be performed according to the following score: 0=absent, 1=induration, 2=severe induration.

The investigator's assessment of general improvement of the target lesion will be performed according to the following score: −1=worsened, 0=no change, 1=mild improvement, 2=moderate improvement, 3=completely healed.

The patients will be asked to assess the global improvement of the target lesion according to the following score: −1=worsened, 0=no change, 1=mild improvement, 2=moderate improvement, 3=completely healed Patients will assess pain and itching in the target lesion using a visual analog scale from 0 to 10.

The invention claimed is:

1. A method of treating cutaneous lupus erythematosus, comprising topically administering to the skin of an individual with cutaneous lupus erythematosus a composition comprising R-salbutamol, a physiologically acceptable derivative thereof, or a pharmaceutically acceptable salt thereof and
   wherein the cutaneous lupus erythematosus is selected from the group consisting of Subacute Cutaneous Lupus Erythematosus, Chronic Cutaneous Lupus Erythematosus, Discoid Lupus Erythematosus, Lupus Panniculitis, and Lupus Erythematosus Profundus.

2. The method according to claim 1, wherein the R-salbutamol is the sole therapeutically active agent in the composition.

3. The method according to claim 1, wherein the composition comprises R-salbutamol in an amount ranging between 0.01 and 10% by weight.

4. The method according to claim 1, wherein the composition comprises R-salbutamol in an amount ranging between 0.2 and 2.5% by weight.

5. The method of claim 1, wherein the individual has cutaneous lupus erythematosus that was not successfully treated by prior therapy.

* * * * *

UNITED STATES PATENT AND TRADEMARK OFFICE
CERTIFICATE OF CORRECTION

PATENT NO. : 8,426,475 B2
APPLICATION NO. : 11/402255
DATED : April 23, 2013
INVENTOR(S) : Morten Sloth Weidner and Hans Christian Wulf It is certified that error appears in the above-identified patent and that said Letters Patent is hereby corrected as shown below:

IN THE SPECIFICATION

Column 1, line 4, please insert the following:
-- CROSS-REFERENCE TO RELATED APPLICATIONS This application claims the benefit of Denmark Application PA 2005 00529 filed, April 13, 2005, which is incorporated herein by reference in its entirety. --

Signed and Sealed this
Eighth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO.         : 8,426,475 B2
APPLICATION NO.    : 11/402255
DATED              : April 23, 2013
INVENTOR(S)        : Morten Sloth Weidner et al.

It is certified that error appears in the above-identified patent and that said Letters Patent is hereby corrected as shown below:

This certificate supersedes the Certificate of Correction issued October 8, 2013.
The certificate is vacated since request for the Certificate of Correction treated as a
petition under 37 CFR 1.55(c), seeking to incorporate by reference the prior-filed
application, was dismissed by the Office of Petitions. The Certificate of
Correction was published in error and should not have been issued for this patent.

Signed and Sealed this
Third Day of December, 2013

Margaret A. Focarino
*Commissioner for Patents of the United States Patent and Trademark Office*

UNITED STATES PATENT AND TRADEMARK OFFICE
CERTIFICATE OF CORRECTION

| | | |
|---|---|---|
| PATENT NO. | : 8,426,475 B2 | |
| APPLICATION NO. | : 11/402255 | |
| DATED | : April 23, 2013 | |
| INVENTOR(S) | : Morten Sloth Weidner et al. | |

It is certified that error appears in the above-identified patent and that said Letters Patent is hereby corrected as shown below:

ON THE TITLE PAGE OF THE PATENT

Please insert the following priority claim on the face of the Patent.

-- (30)   Foreign Application Priority Data

Apr. 13, 2005   (DK) ................ PA 2005 00529 --

IN THE SPECIFICATION

Column 1, line 4, please insert the following:

-- CROSS-REFERENCE TO RELATED APPLICATIONS

This application claims the benefit of Denmark Application PA 2005 00529 filed, April 13, 2005, which is incorporated herein by reference in its entirety. --

Signed and Sealed this
Fourteenth Day of January, 2014

Michelle K. Lee
*Deputy Director of the United States Patent and Trademark Office*